US006251677B1

(12) United States Patent
Wilson et al.

(10) Patent No.: US 6,251,677 B1
(45) Date of Patent: *Jun. 26, 2001

(54) HYBRID ADENOVIRUS-AAV VIRUS AND METHODS OF USE THEREOF

(75) Inventors: James M. Wilson, Gladwyne, PA (US); William M. Kelley, Ann Arbor, MI (US); Krishna J. Fisher, New Orleans, LA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/246,320

(22) Filed: Feb. 8, 1999

Related U.S. Application Data

(63) Continuation of application No. 08/836,087, filed on Aug. 25, 1997, now Pat. No. 5,871,982.

(51) Int. Cl.$^7$ .................. C12N 15/861; C12N 15/864; C12N 5/10; C12N 15/63; A61K 48/00

(52) U.S. Cl. .................. 435/457; 424/93.2; 424/93.6; 435/320.1; 435/325; 435/366; 435/369; 435/456; 435/463; 536/23.1; 536/23.72

(58) Field of Search .................. 435/235.1, 320.1, 435/325, 366, 369, 456, 457, 463, 5, 6; 536/23.1, 23.72; 424/93.2, 93.6

(56) References Cited

U.S. PATENT DOCUMENTS

| | | | |
|---|---|---|---|
| 4,797,368 | 1/1989 | Carter | 435/320.1 |
| 5,139,941 | 8/1992 | Muzyczka | 435/456 |
| 5,166,320 | 11/1992 | Wu | 530/395 |
| 5,173,414 | 12/1992 | Lebkowski | 435/91.4 |
| 5,240,846 | 8/1993 | Collins | 435/371 |
| 5,252,479 | 10/1993 | Srivastava | 435/235.1 |
| 5,354,678 | 10/1994 | Lebkowski | 435/463 |
| 5,436,146 | 7/1995 | Shenk | 435/457 |
| 5,474,935 | 12/1995 | Chatterjee | 435/320.1 |
| 5,478,745 | 12/1995 | Samulski | 435/320.1 |
| 5,622,856 | 4/1997 | Natsoulis | 435/325 |
| 5,753,500 | 5/1998 | Shenk | 435/320.1 |
| 5,756,283 | 5/1998 | Wilson | 435/5 |
| 5,856,152 | 1/1999 | Wilson | 435/457 |
| 5,871,982 | 2/1999 | Wilson | 435/457 |
| 5,872,154 | 2/1999 | Wilson | 514/885 |

FOREIGN PATENT DOCUMENTS

| | | |
|---|---|---|
| WO91/18088 | 11/1991 | (WO) . |
| WO93/24641 | 12/1993 | (WO) . |
| WO94/12649 | 6/1994 | (WO) . |
| WO94/13788 | 6/1994 | (WO) . |
| WO94/17832 | 8/1994 | (WO) . |
| WO95/00655 | 1/1995 | (WO) . |
| WO95/02697 | 1/1995 | (WO) . |
| WO95/20671 | 1/1995 | (WO) . |
| WO95/06743 | 3/1995 | (WO) . |
| WO95/07995 | 3/1995 | (WO) . |
| WO95/13365 | 5/1995 | (WO) . |
| WO95/13392 | 5/1995 | (WO) . |
| WO95/14771 | 6/1995 | (WO) . |
| WO95/23867 | 9/1995 | (WO) . |
| WO95/28493 | 10/1995 | (WO) . |
| WO95/33824 | 12/1995 | (WO) . |
| WO95/34670 | 12/1995 | (WO) . |
| WO96/00587 | 1/1996 | (WO) . |
| WO96/13597 | 5/1996 | (WO) . |
| WO96/13598 | 5/1996 | (WO) . |
| WO96/18727 | 6/1996 | (WO) . |
| WO96/26285 | 8/1996 | (WO) . |
| WO96/39530 | 12/1996 | (WO) . |

OTHER PUBLICATIONS

K. L. Berkner, Current Topics in Microbiology and Immunology, vol. 158, pp. 39–66, 1992.*

Y. Watanabe, "Serial Inbreeding of Rabbits with Hereditary Hyperlipidemia (WHHL–Rabbit)", *Atherosclerosis*, 36:261–268 (Jan., 1980).

K. Tanzawa et al, "WHHL–Rabbit: A Low Density Lipoprotein Receptor–Deficient Animal Model for Familial Hypercholesterolemia", *FEBS Letters*, 118(1):81–84 (Aug., 1980).

J. Goldstein et al, "Defective Lipoprotein Receptors and Atherosclerosis—Lessons from an Animal Counterpart of Familial Hypercholesterolemia", New Engl. J. Med., 309(5):288–296 (Aug. 4, 1983).

S. Ishibashi et al., "Hypercholesterolemia in Low Density Lipoprotein Receptor Knockout Mice and its Reversal by Adenovirus–Mediated Gene Delivery", J. Clin. Invest., 92:883–893 (Aug., 1993) [Ishibashi I].

S. Ishibashi et al, "Massive Xathomatosis and Atherosclerosis in Cholesterol–fed Low Density Lipoprotein Receptor–negative Mice", J. Clin. Invest., 93:1885–1893 (May, 1994) [Ishibashi II].

J. Wilson, "Cystic Fibrosis—Vehicles for Gene Therapy", Nature, 365:691–692 (Oct. 21, 1993) [Wilson I].

M. Horwitz, "Adenoviridae and Their Replication", Virology, 2d edition, ed. B. N. Fields, Raven Press, Ltd., New York, Chapter 60, pp. 1679–1721 (1990).

Y. Yang et al, "Cellular Immunity to Viral Antigens Limits E1–deleted Adenoviruses for Gene Therapy", Proc. Natl. Acad. Sci. USA, 91:4407–4411 (May, 1994).

J. Wilson et al, "Research Article—Transplantation of Allogeneic Hepatocytes into LDL Receptor Deficient Rabbits Leads to Transient Improvement in Hypercholesterolemia", Clin. Bio., 3:21–26 (Feb. 28, 1991) [Wilson II].

(List continued on next page.)

*Primary Examiner*—David Guzo
(74) *Attorney, Agent, or Firm*—Howson and Howson

(57) ABSTRACT

The present invention provides a hybrid vector construct which comprises a portion of an adenovirus, 5' and 3' ITR sequences from an AAV, and a selected transgene. Also provided is a hybrid virus linked via a polycation conjugate to an AAV rep gene to form a single particle. These trans-infection particles are characterized by high titer transgene delivery to a host cell and the ability to stably integrate the transgene into the host cell chromosome. Also disclosed is the use of the hybrid vectors and viruses to produce large quantities of recombinant AAV.

39 Claims, 21 Drawing Sheets

OTHER PUBLICATIONS

M. Grossman et al, "Towards Liver–Directed Gene Therapy: Retrovirus–Mediated Gene Transfer into Human Hepatocytes", Som. Cell. And Mol. Gen., 17(6):601–607 (Nov., 1991).

M. Boshart et al, "A Very Strong Enhancer is Located Upstream of an Immediate Early Gene of Human Cytomegalovirus", Cell, 41:521–530 (Jun., 1985).

K. Kozarsky et al, "In Vivo Correction of Low Density Lipoprotein Receptor Deficiency in the Watanabe Heritage Hyperlipidemic Rabbit with Recombinant Adenoviruses", J. Biol. Chem., 269(18):13695–13702 (May 6, 1994).

C. Laughlin et al, "Cloning of Infectious Adeno–Associated Virus Genomes in Bacterial Plasmids", Gene, 23:65–73 (Jul., 1983).

J. Price et al, "Lineage Analysis in the Vertebrate Nervous System by Retrovirus–Mediated Gene Transfer", Proc. Natl. Acad. Sci. USA, 84:156–160 (Jan., 1987).

J. Wilson et al, "A Novel Mechanism for Achieving Transgene Persistence in Vivo after Somatic Gene Transfer into Hepatocytes", J. Biol. Chem., 267(16):11483–11489 (Jun. 5, 1992) [Wilson III].

T. Kost et al, "The Nucleotide Sequence of the Chick Cytoplasmic β–actin Gene", Nucl. Acids Res., 11(23):8287–8301 (Dec. 11, 1983).

J. Schreiber et al, "Recombinant Retroviruses Containing Novel Reporter Genes", Biotechniques, 14(5):818–823 (May, 1993).

J. Riordan et al, "Identification of the Cystic Fibrosis Gene: Cloning and Characterization of Complementary DNA", Science, 245:1066–1073 (Sep. 8, 1989).

M. Brown et al, "A Receptor–Mediated Pathway for Cholesterol Homeostasis", Science, 212:34–46 (Apr. 4, 1986).

T. Yamamoto et al, "The Human LDL Receptor: A Cysteine–Rich Protein with Multiple Alu Sequences in its mRNA", Cell, 39:27–38 (Nov., 1984).

R. Samulski et al, "Helper–Free Stocks of Recombinant Adeno–Associated Viruses: Normal Integration does not Require Viral Gene Expression", J. Virol., 63(9):3822–3828 (Sep., 1989).

T. Shenk et al, "Genetic Analysis of Adenoviruses", Current Topics In Microbiol. And Immunol., 111:1–39 (1984).

M. Kaplitt et al, "Long–Term Gene Expression and Phenotypic Correction Using Adeno–Associated Virus Vectors in the Mammalian Brain", Nat. Genet., 8;148–154 (Oct., 1994).

D. Russell et al, "Adeno–Associated Virus Vectors Preferentially Transduce Cells in S. Phase", Proc. Natl. Acad. Sci. USA, 91:8915–8919 (Sep., 1994).

J. Wilson et al, "Correction of the Genetic Defect in Hepatocytes for the Watanabe Heritable Hyperlipidemic Rabbit", Proc. Natl. Acad. Sci. USA, 85:4421–4425 (Jun., 1988) [Wilson IV].

C. Wu et al, "Targeting Genes: Delivery and Persistent Expression of a Foreign Gene Driven by Mammalian Regulatory Elements in Vivo", J. Biol. Chem., 264(29):16985–16987 (Oct. 15, 1989).

K. Fisher et al, "Biochemical and Functional Analysis of an Adenovirus–Based Ligand Complex for Gene Transfer", Biochem. J., 229:49–58 (Apr. 1, 1994).

S. Orkin et al, "Report and Recommendations of the Panel to Assess the NIH Investment in Research on Gene Therapy" (Dec. 7, 1995).

* cited by examiner

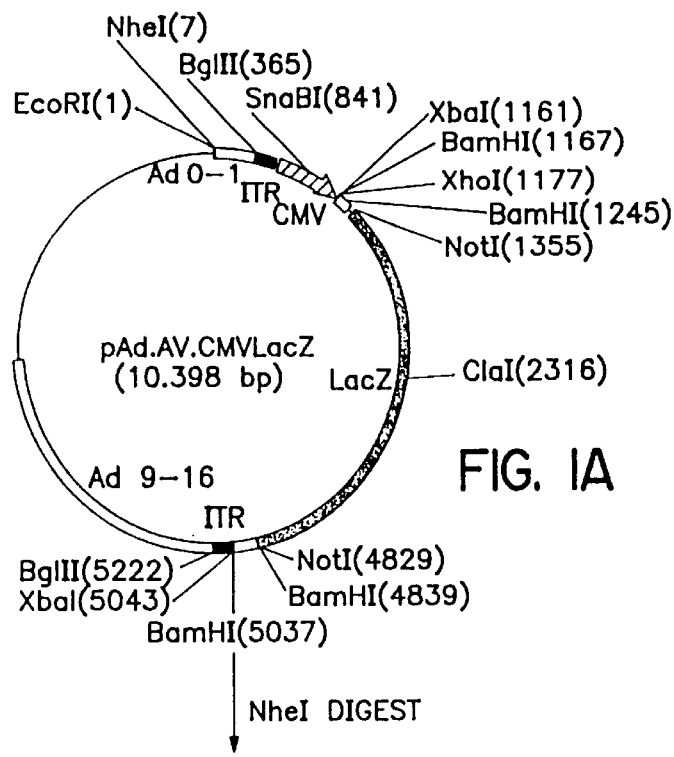
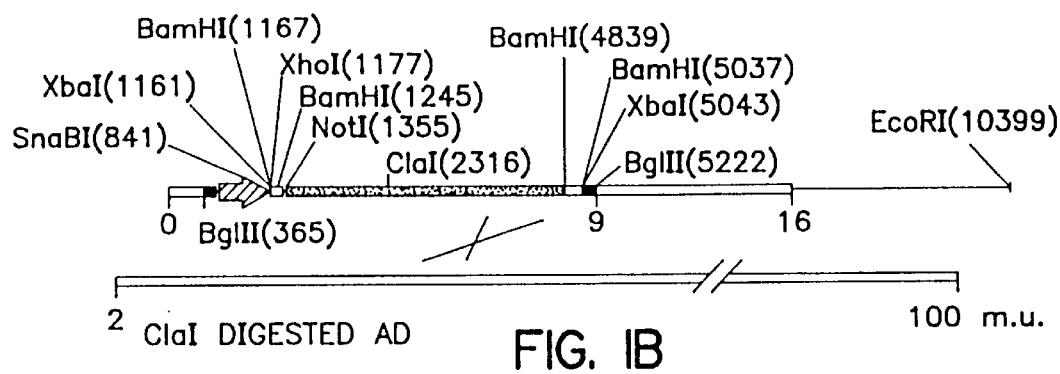
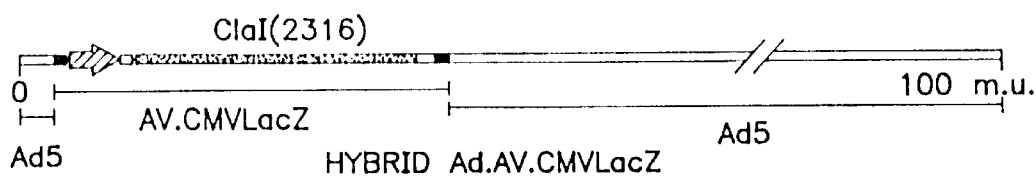

FIGURE 2A

```
GAATTCGCTA GCATCATCAA TAATATACCT TATTTTGGAT TGAAGCCAAT ATGATAATGA
                                                                60
GGGGGTGGAG TTTGTGACGT GGCGCGGGGC GTGGGAACGG GGCGGGTGAC GTAGTAGTGT
                                                               120
GGCGGAAGTG TGATGTTGCA AGTGTGGCGG AACACATGTA AGCGACGGAT GTGGCAAAAG
                                                               180
TGACGTTTTT GGTGTGCGCC GGTGTACACA GGAAGTGACA ATTTTCGCGC GGTTTTAGGC
                                                               240
GGATGTTGTA GTAAATTTGG GCGTAACCGA GTAAGATTTG GCCATTTTCG CGGGAAAACT
                                                               300
GAATAAGAGG AAGTGAAATC TGAATAATTT TGTGTTACTC ATAGCGCGTA ATATTTGTCT
                                                               360
AGGGAGATCT GCTGCGCGCT CGCTCGCTCA CTGAGGCCGC CCGGGCAAAG CCCGGGCGTC
                                                               420
GGGCGACCTT TGGTCGCCCG GCCTCAGTGA GCGAGCGAGC GCGCAGAGAG GGAGTGGCCA
                                                               480
ACTCCATCAC TAGGGGTTCC TTGTAGTTAA TGATTAACCC GCCATGCTAC TTATCTACAA
                                                               540
TTCGAGCTTG CATGCCTGCA GGTCGTTACA TAACTTACGG TAAATGGCCC GCCTGGCTGA
                                                               600
CCGCCCAACG ACCCCGCCC ATTGACGTCA ATAATGACGT ATGTTCCCAT AGTAACGCCA
                                                               660
ATAGGGACTT TCCATTGACG TCAATGGGTG GAGTATTTAC GGTAAACTGC CCACTTGGCA
                                                               720
GTACATCAAG TGTATCATAT GCCAAGTACG CCCCTATTG ACGTCAATGA CGGTAAATGG
                                                               780
CCCGCCTGGC ATTATGCCCA GTACATGACC TTATGGGACT TTCCTACTTG GCAGTACATC
                                                               840
TACGTATTAG TCATCGCTAT TACCATGGTG ATGCGGTTTT GGCAGTACAT CAATGGGCGT
                                                               900
GGATAGCGGT TTGACTCACG GGGATTTCCA AGTCTCCACC CCATTGACGT CAATGGGAGT
                                                               960
TTGTTTTGGC ACCAAAATCA ACGGGACTTT CCAAAATGTC GTAACAACTC CGCCCCATTG
                                                              1020
```

FIGURE 2B

```
ACGCAAATGG GCGGTAGGCG TGTACGGTGG GAGGTCTATA TAAGCAGAGC TCGTTTAGTG
                                                                1080

AACCGTCAGA TCGCCTGGAG ACGCCATCCA CGCTGTTTTG ACCTCCATAG AAGACACCGG
                                                                1140

GACCGATCCA GCCTCCGGAC TCTAGAGGAT CCGGTACTCG AGGAACTGAA AAACCAGAAA
                                                                1200

GTTAACTGGT AAGTTTAGTC TTTTTGTCTT TTATTTCAGG TCCCGGATCC GGTGGTGGTG
                                                                1260

CAAATCAAAG AACTGCTCCT CAGTGGATGT TGCCTTTACT TCTAGGCCTG TACGGAAGTG
                                                                1320

TTACTTCTGC TCTAAAAGCT GCGGAATTGT ACCCGCGGCC GCAATTCCCG GGATCGAAA
                                                                1380

GAGCCTGCTA AAGCAAAAAA GAAGTCACCA TGTCGTTTAC TTTGACCAAC AAGAACGTGA
                                                                1440

TTTTCGTTGC CGGTCTGGGA GGCATTGGTC TGGACACCAG CAAGGAGCTG CTCAAGCGCG
                                                                1500

ATCCCGTCGT TTTACAACGT CGTGACTGGG AAAACCCTGG CGTTACCCAA CTTAATCGCC
                                                                1560

TTGCAGCACA TCCCCCTTTC GCCAGCTGGC GTAATAGCGA AGAGGCCCGC ACCGATCGCC
                                                                1620

CTTCCCAACA GTTGCGCAGC CTGAATGGCG AATGGCGCTT TGCCTGGTTT CCGGCACCAG
                                                                1680

AAGCGGTGCC GGAAAGCTGG CTGGAGTGCG ATCTTCCTGA GGCCGATACT GTCGTCGTCC
                                                                1740

CCTCAAACTG GCAGATGCAC GGTTACGATG CGCCCATCTA CACCAACGTA ACCTATCCCA
                                                                1800

TTACGGTCAA TCCGCCGTTT GTTCCCACGG AGAATCCGAC GGGTTGTTAC TCGCTCACAT
                                                                1860

TTAATGTTGA TGAAAGCTGG CTACAGGAAG GCCAGACGCG AATTATTTTT GATGGCGTTA
                                                                1920

ACTCGGCGTT TCATCTGTGG TGCAACGGGC GCTGGGTCGG TTACGGCCAG GACAGTCGTT
                                                                1980

TGCCGTCTGA ATTTGACCTG AGCGCATTTT TACGCGCCGG AGAAACCGC CTCGCGGTGA
                                                                2040
```

FIGURE 2C

```
TGGTGCTGCG TTGGAGTGAC GGCAGTTATC TGGAAGATCA GGATATGTGG CGGATGAGCG
                                                                2100
GCATTTTCCG TGACGTCTCG TTGCTGCATA AACCGACTAC ACAAATCAGC GATTTCCATG
                                                                2160
TTGCCACTCG CTTTAATGAT GATTTCAGCC GCGCTGTACT GGAGGCTGAA GTTCAGATGT
                                                                2220
GCGGCGAGTT GCGTGACTAC CTACGGGTAA CAGTTTCTTT ATGGCAGGGT GAAACGCAGG
                                                                2280
TCGCCAGCGG CACCGCGCCT TTCGGCGGTG AAATTATCGA TGAGCGTGGT GGTTATGCCG
                                                                2340
ATCGCGTCAC ACTACGTCTG AACGTCGAAA ACCCGAAACT GTGGAGCGCC GAAATCCCGA
                                                                2400
ATCTCTATCG TGCGGTGGTT GAACTGCACA CCGCCGACGG CACGCTGATT GAAGCAGAAG
                                                                2460
CCTGCGATGT CGGTTTCCGC GAGGTGCGGA TTGAAAATGG TCTGCTGCTG CTGAACGGCA
                                                                2520
AGCCGTTGCT GATTCGAGGC GTTAACCGTC ACGAGCATCA TCCTCTGCAT GGTCAGGTCA
                                                                2580
TGGATGAGCA GACGATGGTG CAGGATATCC TGCTGATGAA GCAGAACAAC TTTAACGCCG
                                                                2640
TGCGCTGTTC GCATTATCCG AACCATCCGC TGTGGTACAC GCTGTGCGAC CGCTACGGCC
                                                                2700
TGTATGTGGT GGATGAAGCC AATATTGAAA CCCACGGCAT GGTGCCAATG AATCGTCTGA
                                                                2760
CCGATGATCC GCGCTGGCTA CCGGCGATGA GCAACGCGT AACGCGAATG GTGCAGCGCG
                                                                2820
ATCGTAATCA CCCGAGTGTG ATCATCTGGT CGCTGGGGAA TGAATCAGGC CACGGCGCTA
                                                                2880
ATCACGACGC GCTGTATCGC TGGATCAAAT CTGTCGATCC TTCCCGCCCG GTGCAGTATG
                                                                2940
AAGGCGGCGG AGCCGACACC ACGGCCACCG ATATTATTTG CCCGATGTAC GCGCGCGTGG
                                                                3000
ATGAAGACCA GCCCTTCCCG GCTGTGCCGA AATGGTCCAT CAAAAAATGG CTTTCGCTAC
                                                                3060
```

FIGURE 2D

```
CTGGAGAGAC GCGCCCGCTG ATCCTTTGCG AATACGCCCA CGCGATGGGT AACAGTCTTG
                                                               3120

GCGGTTTCGC TAAATACTGG CAGGCGTTTC GTCAGTATCC CCGTTTACAG GGCGGCTTCG
                                                               3180

TCTGGGACTG GGTGGATCAG TCGCTGATTA AATATGATGA AAACGGCAAC CCGTGGTCGG
                                                               3240

CTTACGGCGG TGATTTTGGC GATACGCCGA ACGATCGCCA GTTCTGTATG AACGGTCTGG
                                                               3300

TCTTTGCCGA CCGCACGCCG CATCCAGCGC TGACGGAAGC AAAACACCAG CAGCAGTTTT
                                                               3360

TCCAGTTCCG TTTATCCGGG CAAACCATCG AAGTGACCAG CGAATACCTG TTCCGTCATA
                                                               3420

GCGATAACGA GCTCCTGCAC TGGATGGTGG CGCTGGATGG TAAGCCGCTG GCAAGCGGTG
                                                               3480

AAGTGCCTCT GGATGTCGCT CCACAAGGTA AACAGTTGAT TGAACTGCCT GAACTACCGC
                                                               3540

AGCCGGAGAG CGCCGGGCAA CTCTGGCTCA CAGTACGCGT AGTGCAACCG AACGCGACCG
                                                               3600

CATGGTCAGA AGCCGGGCAC ATCAGCGCCT GGCAGCAGTG GCGTCTGGCG GAAAACCTCA
                                                               3660

GTGTGACGCT CCCCGCCGCG TCCCACGCCA TCCCGCATCT GACCACCAGC GAAATGGATT
                                                               3720

TTTGCATCGA GCTGGGTAAT AAGCGTTGGC AATTTAACCG CCAGTCAGGC TTTCTTTCAC
                                                               3780

AGATGTGGAT TGGCGATAAA AAACAACTGC TGACGCCGCT GCGCGATCAG TTCACCCGTG
                                                               3840

CACCGCTGGA TAACGACATT GGCGTAAGTG AAGCGACCCG CATTGACCCT AACGCCTGGG
                                                               3900

TCGAACGCTG GAAGGCGGCG GGCCATTACC AGGCCGAAGC AGCGTTGTTG CAGTGCACGG
                                                               3960

CAGATACACT TGCTGATGCG GTGCTGATTA CGACCGCTCA CGCGTGGCAG CATCAGGGGA
                                                               4020

AAACCTTATT TATCAGCCGG AAAACCTACC GGATTGATGG TAGTGGTCAA ATGGCGATTA
                                                               4080
```

FIGURE 2E

```
CCGTTGATGT TGAAGTGGCG AGCGATACAC CGCATCCGGC GCGGATTGGC CTGAACTGCC
                                                                 4140

AGCTGGCGCA GGTAGCAGAG CGGGTAAACT GGCTCGGATT AGGGCCGCAA GAAAACTATC
                                                                 4200

CCGACCGCCT TACTGCCGCC TGTTTTGACC GCTGGGATCT GCCATTGTCA GACATGTATA
                                                                 4260

CCCCGTACGT CTTCCCGAGC GAAAACGGTC TGCGCTGCGG GACGCGCGAA TTGAATTATG
                                                                 4320

GCCCACACCA GTGGCGCGGC GACTTCCAGT TCAACATCAG CCGCTACAGT CAACAGCAAC
                                                                 4380

TGATGGAAAC CAGCCATCGC CATCTGCTGC ACGCGGAAGA AGGCACATGG CTGAATATCG
                                                                 4440

ACGGTTTCCA TATGGGGATT GGTGGCGACG ACTCCTGGAG CCCGTCAGTA TCGGCGGAAT
                                                                 4500

TACAGCTGAG CGCCGGTCGC TACCATTACC AGTTGGTCTG GTGTCAAAAA TAATAATAAC
                                                                 4560

CGGGCAGGCC ATGTCTGCCC GTATTTCGCG TAAGGAAATC CATTATGTAC TATTTAAAAA
                                                                 4620

ACACAAACTT TTGGATGTTC GGTTTATTCT TTTTCTTTTA CTTTTTTATC ATGGGAGCCT
                                                                 4680

ACTTCCCGTT TTTCCCGATT TGGCTACATG ACATCAACCA TATCAGCAAA AGTGATACGG
                                                                 4740

GTATTATTTT TGCCGCTATT TCTCTGTTCT CGCTATTATT CCAACCGCTG TTTGGTCTGC
                                                                 4800

TTTCTGACAA ACTCGGCCTC GACTCTAGGC GGCCGCGGGG ATCCAGACAT GATAAGATAC
                                                                 4860

ATTGATGAGT TTGGACAAAC CACAACTAGA ATGCAGTGAA AAAAATGCTT TATTTGTGAA
                                                                 4920

ATTTGTGATG CTATTGCTTT ATTTGTAACC ATTATAAGCT GCAATAAACA AGTTAACAAC
                                                                 4980

AACAATTGCA TTCATTTTAT GTTTCAGGTT CAGGGGGAGG TGTGGGAGGT TTTTTCGGAT
                                                                 5040

CCTCTAGAGT CGAGTAGATA AGTAGCATGG CGGGTTAATC ATTAACTACA AGGAACCCCT
                                                                 5100
```

FIGURE 2F

```
AGTGATGGAG TTGGCCACTC CCTCTCTGCG CGCTCGCTCG CTCACTGAGG CCGGGCGACC
                                                                 5160

AAAGGTCGCC CGACGCCCGG GCTTTGCCCG GCGGCCTCA GTGAGCGAGC GAGCGCGCAG
                                                                 5220

CAGATCTGGA AGGTGCTGAG GTACGATGAG ACCCGCACCA GGTGCAGACC CTGCGAGTGT
                                                                 5280

GGCGGTAAAC ATATTAGGAA CCAGCCTGTG ATGCTGGATG TGACCGAGGA GCTGAGGCCC
                                                                 5340

GATCACTTGG TGCTGGCCTG CACCCGCGCT GAGTTTGGCT CTAGCGATGA AGATACAGAT
                                                                 5400

TGAGGTACTG AAATGTGTGG GCGTGGCTTA AGGGTGGGAA AGAATATATA AGGTGGGGGT
                                                                 5460

CTTATGTAGT TTTGTATCTG TTTTGCAGCA GCCGCCGCCG CCATGAGCAC CAACTCGTTT
                                                                 5520

GATGGAAGCA TTGTGAGCTC ATATTTGACA ACGCGCATGC CCCCATGGGC CGGGGTGCGT
                                                                 5580

CAGAATGTGA TGGGCTCCAG CATTGATGGT CGCCCCGTCC TGCCCGCAAA CTCTACTACC
                                                                 5640

TTGACCTACG AGACCGTGTC TGGAACGCCG TTGGAGACTG CAGCCTCCGC CGCCGCTTCA
                                                                 5700

GCCGCTGCAG CCACCGCCCG CGGGATTGTG ACTGACTTTG CTTTCCTGAG CCCGCTTGCA
                                                                 5760

AGCAGTGCAG CTTCCCGTTC ATCCGCCCGC GATGACAAGT TGACGGCTCT TTTGGCACAA
                                                                 5820

TTGGATTCTT TGACCCGGGA ACTTAATGTC GTTTCTCAGC AGCTGTTGGA TCTGCGCCAG
                                                                 5880

CAGGTTTCTG CCCTGAAGGC TTCCTCCCCT CCCAATGCGG TTTAAAACAT AAATAAAAAA
                                                                 5940

CCAGACTCTG TTTGGATTTG GATCAAGCAA GTGTCTTGCT GTCTTTATTT AGGGGTTTTG
                                                                 6000

CGCGCGCGGT AGGCCCGGGA CCAGCGGTCT CGGTCGTTGA GGGTCCTGTG TATTTTTTCC
                                                                 6060

AGGACGTGGT AAAGGTGACT CTGGATGTTC AGATACATGG GCATAAGCCC GTCTCTGGGG
                                                                 6120
```

FIGURE 2G

```
TGGAGGTAGC ACCACTGCAG AGCTTCATGC TGCGGGGTGG TGTTGTAGAT GATCCAGTCG
                                                              6180

TAGCAGGAGC GCTGGGCGTG GTGCCTAAAA ATGTCTTTCA GTAGCAAGCT GATTGCCAGG
                                                              6240

GGCAGGCCCT TGGTGTAAGT GTTTACAAAG CGGTTAAGCT GGGATGGGTG CATACGTGGG
                                                              6300

GATATGAGAT GCATCTTGGA CTGTATTTTT AGGTTGGCTA TGTTCCCAGC CATATCCCTC
                                                              6360

CGGGGATTCA TGTTGTGCAG AACCACCAGC ACAGTGTATC CGGTGCACTT GGGAAATTTG
                                                              6420

TCATGTAGCT TAGAAGGAAA TGCGTGGAAG AACTTGGAGA CGCCCTTGTG ACCTCCAAGA
                                                              6480

TTTTCCATGC ATTCGTCCAT AATGATGGCA ATGGGCCCAC GGGCGGCGGC CTGGGCGAAG
                                                              6540

ATATTTCTGG GATCACTAAC GTCATAGTTG TGTTCCAGGA TGAGATCGTC ATAGGCCATT
                                                              6600

TTTACAAAGC GCGGGCGGAG GGTGCCAGAC TGCGGTATAA TGGTTCCATC CGGCCCAGGG
                                                              6660

GCGTAGTTAC CCTCACAGAT TTGCATTTCC CACGCTTTGA GTTCAGATGG GGGGATCATG
                                                              6720

TCTACCTGCG GGGCGATGAA GAAAACGGTT TCCGGGGTAG GGGAGATCAG CTGGGAAGAA
                                                              6780

AGCAGGTTCC TGAGCAGCTG CGACTTACCG CAGCCGGTGG GCCCGTAAAT CACACCTATT
                                                              6840

ACCGGGTGCA ACTGGTAGTT AAGAGAGCTG CAGCTGCCGT CATCCCTGAG CAGGGGGGCC
                                                              6900

ACTTCGTTAA GCATGTCCCT GACTCGCATG TTTTCCCTGA CCAAATCCGC CAGAAGGCGC
                                                              6960

TCGCCGCCCA GCGATAGCAG TTCTTGCAAG GAAGCAAAGT TTTTCAACGG TTTGAGACCG
                                                              7020

TCCGCCGTAG GCATGCTTTT GAGCGTTTGA CCAAGCAGTT CCAGGCGGTC CCACAGCTCG
                                                              7080

GTCACCTGCT CTACGGCATC TCGATCCAGC ATATCTCCTC GTTTCGCGGG TTGGGGCGGC
                                                              7140
```

FIGURE 2H

```
TTTCGCTGTA CGGCAGTAGT CGGTGCTCGT CCAGACGGGC CAGGGTCATG TCTTTCCACG
                                                                7200
GGCGCAGGGT CCTCGTCAGC GTAGTCTGGG TCACGGTGAA GGGGTGCGCT CCGGGCTGCG
                                                                7260
CGCTGGCCAG GGTGCGCTTG AGGCTGGTCC TGCTGGTGCT GAAGCGCTGC CGGTCTTCGC
                                                                7320
CCTGCGCGTC GGCCAGGTAG CATTTGACCA TGGTGTCATA GTCCAGCCCC TCCGCGGCGT
                                                                7380
GGCCCTTGGC GCGCAGCTTG CCCTTGGAGG AGGCGCCGCA CGAGGGGCAG TGCAGACTTT
                                                                7440
TGAGGGCGTA GAGCTTGGGC GCGAGAAATA CCGATTCCGG GGAGTAGGCA TCCGCGCCGC
                                                                7500
AGGCCCCGCA GACGGTCTCG CATTCCACGA GCCAGGTGAG CTCTGGCCGT TCGGGGTCAA
                                                                7560
AAACCAGGTT TCCCCCATGC TTTTTGATGC GTTTCTTACC TCTGGTTTCC ATGAGCCGGT
                                                                7620
GTCCACGCTC GGTGACGAAA AGGCTGTCCG TGTCCCCGTA TACAGACTTG AGAGGCCTGT
                                                                7680
CCTCGACCGA TGCCCTTGAG AGCCTTCAAC CCAGTCAGCT CCTTCCGGTG GGCGCGGGGC
                                                                7740
ATGACTATCG TCGCCGCACT TATGACTGTC TTCTTTATCA TGCAACTCGT AGGACAGGTG
                                                                7800
CCGGCAGCGC TCTGGGTCAT TTTCGGCGAG GACCGCTTTC GCTGGAGCGC GACGATGATC
                                                                7860
GGCCTGTCGC TTGCGGTATT CGGAATCTTG CACGCCCTCG CTCAAGCCTT CGTCACTGGT
                                                                7920
CCCGCCACCA AACGTTTCGG CGAGAAGCAG GCCATTATCG CCGGCATGGC GGCCGACGCG
                                                                7980
CTGGGCTACG TCTTGCTGGC GTTCGCGACG CGAGGCTGGA TGGCCTTCCC CATTATGATT
                                                                8040
CTTCTCGCTT CCGGCGGCAT CGGGATGCCC GCGTTGCAGG CCATGCTGTC CAGGCAGGTA
                                                                8100
GATGACGACC ATCAGGGACA GCTTCAAGGA TCGCTCGCGG CTCTTACCAG CCTAACTTCG
                                                                8160
```

FIGURE 21

```
ATCACTGGAC CGCTGATCGT CACGGCGATT TATGCCGCCT CGGCGAGCAC ATGGAACGGG
                                                               8220
TTGGCATGGA TTGTAGGCGC CGCCCTATAC CTTGTCTGCC TCCCCGCGTT GCGTCGCGGT
                                                               8280
GCATGGAGCC GGGCCACCTC GACCTGAATG GAAGCCGGCG GCACCTCGCT AACGGATTCA
                                                               8340
CCACTCCAAG AATTGGAGCC AATCAATTCT TGCGGAGAAC TGTGAATGCG CAAACCAACC
                                                               8400
CTTGGCAGAA CATATCCATC GCGTCCGCCA TCTCCAGCAG CCGCACGCGG CGCATCTCGG
                                                               8460
GCAGCGTTGG GTCCTGGCCA CGGGTGCGCA TGATCGTGCT CCTGTCGTTG AGGACCCGGC
                                                               8520
TAGGCTGGCG GGGTTGCCTT ACTGGTTAGC AGAATGAATC ACCGATACGC GAGCGAACGT
                                                               8580
GAAGCGACTG CTGCTGCAAA ACGTCTGCGA CCTGAGCAAC AACATGAATG GTCTTCGGTT
                                                               8640
TCCGTGTTTC GTAAAGTCTG GAAACGCGGA AGTCAGCGCC CTGCACCATT ATGTTCCGGA
                                                               8700
TCTGCATCGC AGGATGCTGC TGGCTACCCT GTGGAACACC TACATCTGTA TTAACGAAGC
                                                               8760
CTTTCTCAAT GCTCACGCTG TAGGTATCTC AGTTCGGTGT AGGTCGTTCG CTCCAAGCTG
                                                               8820
GGCTGTGTGC ACGAACCCCC CGTTCAGCCC GACCGCTGCG CCTTATCCGG TAACTATCGT
                                                               8880
CTTGAGTCCA ACCCGGTAAG ACACGACTTA TCGCCACTGG CAGCAGCCAC TGGTAACAGG
                                                               8940
ATTAGCAGAG CGAGGTATGT AGGCGGTGCT ACAGAGTTCT TGAAGTGGTG GCCTAACTAC
                                                               9000
GGCTACACTA GAAGGACAGT ATTTGGTATC TGCGCTCTGC TGAAGCCAGT TACCTTCGGA
                                                               9060
AAAAGAGTTG GTAGCTCTTG ATCCGGCAAA CAAACCACCG CTGGTAGCGG TGGTTTTTTT
                                                               9120
GTTTGCAAGC AGCAGATTAC GCGCAGAAAA AAAGGATCTC AAGAAGATCC TTTGATCTTT
                                                               9180
```

FIGURE 2J

```
TCTACGGGGT CTGACGCTCA GTGGAACGAA AACTCACGTT AAGGGATTTT GGTCATGAGA
                                                                9240
TTATCAAAAA GGATCTTCAC CTAGATCCTT TTAAATTAAA AATGAAGTTT TAAATCAATC
                                                                9300
TAAAGTATAT ATGAGTAAAC TTGGTCTGAC AGTTACCAAT GCTTAATCAG TGAGGCACCT
                                                                9360
ATCTCAGCGA TCTGTCTATT TCGTTCATCC ATAGTTGCCT GACTCCCCGT CGTGTAGATA
                                                                9420
ACTACGATAC GGGAGGGCTT ACCATCTGGC CCCAGTGCTG CAATGATACC GCGAGACCCA
                                                                9480
CGCTCACCGG CTCCAGATTT ATCAGCAATA AACCAGCCAG CCGGAAGGGC CGAGCGCAGA
                                                                9540
AGTGGTCCTG CAACTTTATC CGCCTCCATC CAGTCTATTA ATTGTTGCCG GGAAGCTAGA
                                                                9600
GTAAGTAGTT CGCCAGTTAA TAGTTTGCGC AACGTTGTTG CCATTGCTGC AGGCATCGTG
                                                                9660
GTGTCACGCT CGTCGTTTGG TATGGCTTCA TTCAGCTCCG GTTCCCAACG ATCAAGGCGA
                                                                9720
GTTACATGAT CCCCCATGTT GTGCAAAAAA GCGGTTAGCT CCTTCGGTCC TCCGATCGTT
                                                                9780
GTCAGAAGTA AGTTGGCCGC AGTGTTATCA CTCATGGTTA TGGCAGCACT GCATAATTCT
                                                                9840
CTTACTGTCA TGCCATCCGT AAGATGCTTT TCTGTGACTG GTGAGTACTC AACCAAGTCA
                                                                9900
TTCTGAGAAT AGTGTATGCG GCGACCGAGT TGCTCTTGCC CGGCGTCAAC ACGGGATAAT
                                                                9960
ACCGCGCCAC ATAGCAGAAC TTTAAAAGTG CTCATCATTG GAAAACGTTC TTCGGGGCGA
                                                                10020
AAACTCTCAA GGATCTTACC GCTGTTGAGA TCCAGTTCGA TGTAACCCAC TCGTGCACCC
                                                                10080
AACTGATCTT CAGCATCTTT TACTTTCACC AGCGTTTCTG GGTGAGCAAA AACAGGAAGG
                                                                10140
CAAAATGCCG CAAAAAAGGG AATAAGGGCG ACACGGAAAT GTTGAATACT CATACTCTTC
                                                                10200
```

FIGURE 2K

```
CTTTTTCAAT ATTATTGAAG CATTTATCAG GGTTATTGTC TCATGAGCGG ATACATATTT
                                                                10260

GAATGTATTT AGAAAAATAA ACAAATAGGG GTTCCGCGCA CATTTCCCCG AAAAGTGCCA
                                                                10320

CCTGACGTCT AAGAAACCAT TATTATCATG ACATTAACCT ATAAAAATAG GCGTATCACG
                                                                10380

AGGCCCTTTC GTCTTCAA
            10398
```

FIGURE 5A

```
TCGCGCGTTT CGGTGATGAC GGTGAAAACC TCTGACACAT GCAGCTCCCG GAGACGGTCA
                                                                60

CAGCTTGTCT GTAAGCGGAT GCCGGGAGCA GACAAGCCCG TCAGGGCGCG TCAGCGGGTG
                                                               120

TTGGCGGGTG TCGGGGCTGG CTTAACTATG CGGCATCAGA GCAGATTGTA CTGAGAGTGC
                                                               180

ACCATATGCG GTGTGAAATA CCGCACAGAT GCGTAAGGAG AAAATACCGC ATCAGGCGCC
                                                               240

ATTCGCCATT CAGGCTGCGC AACTGTTGGG AAGGGCGATC GGTGCGGGCC TCTTCGCTAT
                                                               300

TACGCCAGCT GGCGAAAGGG GGATGTGCTG CAAGGCGATT AAGTTGGGTA ACGCCAGGGT
                                                               360

TTTCCCAGTC ACGACGTTGT AAAACGACGG CCAGTGCCAA GCTTGCATGC CTGCAGGTCG
                                                               420

ACTCTAGAGG ATCCGAAAAA ACCTCCCACA CCTCCCCCTG AACCTGAAAC ATAAAATGAA
                                                               480

TGCAATTGTT GTTGTTAACT TGTTTATTGC AGCTTATAAT GGTTACAAAT AAAGCAATAG
                                                               540

CATCACAAAT TTCACAAATA AAGCATTTTT TCACTGCAT TCTAGTTGTG GTTTGTCCAA
                                                               600

ACTCATCAAT GTATCTTATC ATGTCTGGAT CCCCGCGGCC GCCAAATCAT TTATTGTTCA
                                                               660

AAGATGCAGT CATCCAAATC CACATTGACC AGATCGCAGG CAGTGCAAGC GTCTGGCACC
                                                               720

TTTCCCATGA TATGATGAAT GTAGCACAGT TTCTGATACG CCTTTTTGAC GACAGAAACG
                                                               780

GGTTGAGATT CTGACACGGG AAAGCACTCT AAACAGTCTT TCTGTCCGTG AGTGAAGCAG
                                                               840

ATATTTGAAT TCTGATTCAT TCTCTCGCAT TGTCTGCAGG GAAACAGCAT CAGATTCATG
                                                               900

CCCACGTGAC GAGAACATTT GTTTTGGTAC CTGTCTGCGT AGTTGATCGA AGCTTCCGCG
                                                               960

TCTGACGTCG ATGGCTGCGC AACTGACTCG CGCACCCGTT TGGGCTCACT TATATCTGCG
                                                              1020
```

FIGURE 5B

```
TCACTGGGGG CGGGTCTTTT CTTGGCTCCA CCCTTTTTGA CGTAGAATTC ATGCTCCACC
                                                                1080

TCAACCACGT GATCCTTTGC CCACCGGAAA AAGTCTTTGA CTTCCTGCTT GGTGACCTTC
                                                                1140

CCAAAGTCAT GATCCAGACG GCGGGTGAGT TCAAATTTGA ACATCCGGTC TTGCAACGGC
                                                                1200

TGCTGGTGTT CGAAGGTCGT TGAGTTCCCG TCAATCACGG CGCACATGTT GGTGTTGGAG
                                                                1260

GTGACGATCA CGGGAGTCGG GTCTATCTGG GCCGAGGACT TGCATTTCTG GTCCACGCGC
                                                                1320

ACCTTGCTTC CTCCGAGAAT GGCTTTGGCC GACTCCACGA CCTTGGCGGT CATCTTCCCC
                                                                1380

TCCTCCCACC AGATCACCAT CTTGTCGACA CAGTCGTTGA AGGGAAAGTT CTCATTGGTC
                                                                1440

CAGTTTACGC ACCCGTAGAA GGGCACAGTG TGGGCTATGG CCTCCGCGAT GTTGGTCTTC
                                                                1500

CCGGTAGTTG CAGGCCCAAA CAGCCAGATG GTGTTCCTCT TGCCGAACTT TTTCGTGGCC
                                                                1560

CATCCCAGAA AGACGGAAGC CGCATATTGG GGATCGTACC CGTTTAGTTC CAAAATTTTA
                                                                1620

TAAATCCGAT TGCTGGAAAT GTCCTCCACG GGCTGCTGGC CCACCAGGTA GTCGGGGGCG
                                                                1680

GTTTTAGTCA GGCTCATAAT CTTTCCCGCA TTGTCCAAGG CAGCCTTGAT TTGGGACCGC
                                                                1740

GAGTTGGAGG CCGCATTGAA GGAGATGTAT GAGGCCTGGT CCTCCTGGAT CCACTGCTTC
                                                                1800

TCCGAGGTAA TCCCCTTGTC CACGAGCCAC CCGACCAGCT CCATGTACCT GGCTGAAGTT
                                                                1860

TTTGATCTGA TCACCGGCGC ATCAGAATTG GGATTCTGAT TCTCTTTGTT CTGCTCCTGC
                                                                1920

GTCTGCGACA CGTGCGTCAG ATGCTGCGCC ACCAACCGTT TACGCTCCGT GAGATTCAAA
                                                                1980

CAGGCGCTTA AATACTGTTC CATATTAGTC CACGCCCACT GGAGCTCAGG CTGGGTTTTG
                                                                2040
```

FIGURE 5C

```
GGGAGCAAGT AATTGGGGAT GTAGCACTCA TCCACCACCT TGTTCCCGCC TCCGGCGCCA
                                                                2100
TTTCTGGTCT TTGTGACCGC GAACCAGTTT GGCAAAGTCG GCTCGATCCC GCGGTAAATT
                                                                2160
CTCTGAATCA GTTTTTCGCG AATCTGACTC AGGAAACGTC CCAAAACCAT GGATTTCACC
                                                                2220
CCGGTGGTTT CCACGAGCAC GTGCATGTGG AAGTAGCTCT CTCCCTTCTC AAATTGCACA
                                                                2280
AAGAAAAGGG CCTCCGGGGC CTTACTCACA CGGCGCCATT CCGTCAGAAA GTCGCGCTGC
                                                                2340
AGCTTCTCGG CCACGGTCAG GGGTGCCTGC TCAATCAGAT TCAGATCCAT GTCAGAATCT
                                                                2400
GGCGGCAACT CCCATTCCTT CTCGGCCACC CAGTTCACAA AGCTGTCAGA AATGCCGGGC
                                                                2460
AGATGCCCGT CAAGGTCGCT GGGGACCTTA ATCACAATCT CGTAAAACCC CGGCATGGCG
                                                                2520
GCTGCGCGTT CAAACCTCCC GCTTCAAAAT GGAGACCCTG CGTGCTCACT CGGGCTTAAA
                                                                2580
TACCCAGCGT GACCACATGG TGTCGCAAAA TGTCGCAAAA CACTCACGTG ACCTCTAATA
                                                                2640
CAGGACTCTA GAGGATCCCC GGGTACCGAG CTCGAATTCG TAATCATGGT CATAGCTGTT
                                                                2700
TCCTGTGTGA AATTGTTATC CGCTCACAAT TCCACACAAC ATACGAGCCG GAAGCATAAA
                                                                2760
GTGTAAAGCC TGGGGTGCCT AATGAGTGAG CTAACTCACA TTAATTGCGT TGCGCTCACT
                                                                2820
GCCCGCTTTC CAGTCGGGAA ACCTGTCGTG CCAGCTGCAT TAATGAATCG GCCAACGCGC
                                                                2880
GGGGAGAGGC GGTTTGCGTA TTGGGCGCTC TTCCGCTTCC TCGCTCACTG ACTCGCTGCG
                                                                2940
CTCGGTCGTT CGGCTGCGGC GAGCGGTATC AGCTCACTCA AAGGCGGTAA TACGGTTATC
                                                                3000
CACAGAATCA GGGGATAACG CAGGAAAGAA CATGTGAGCA AAAGGCCAGC AAAAGGCCAG
                                                                3060
```

FIGURE 5D

```
GAACCGTAAA AAGGCCGCGT TGCTGGCGTT TTTCCATAGG CTCCGCCCCC CTGACGAGCA
                                                                3120

TCACAAAAAT CGACGCTCAA GTCAGAGGTG GCGAAACCCG ACAGGACTAT AAAGATACCA
                                                                3180

GGCGTTTCCC CCTGGAAGCT CCCTCGTGCG CTCTCCTGTT CCGACCCTGC CGCTTACCGG
                                                                3240

ATACCTGTCC GCCTTTCTCC CTTCGGGAAG CGTGGCGCTT TCTCATAGCT CACGCTGTAG
                                                                3300

GTATCTCAGT TCGGTGTAGG TCGTTCGCTC CAAGCTGGGC TGTGTGCACG AACCCCCCGT
                                                                3360

TCAGCCCGAC CGCTGCGCCT TATCCGGTAA CTATCGTCTT GAGTCCAACC CGGTAAGACA
                                                                3420

CGACTTATCG CCACTGGCAG CAGCCACTGG TAACAGGATT AGCAGAGCGA GGTATGTAGG
                                                                3480

CGGTGCTACA GAGTTCTTGA AGTGGTGGCC TAACTACGGC TACACTAGAA GGACAGTATT
                                                                3540

TGGTATCTGC GCTCTGCTGA AGCCAGTTAC CTTCGGAAAA AGAGTTGGTA GCTCTTGATC
                                                                3600

CGGCAAACAA ACCACCGCTG GTAGCGGTGG TTTTTTTGTT TGCAAGCAGC AGATTACGCG
                                                                3660

CAGAAAAAAA GGATCTCAAG AAGATCCTTT GATCTTTTCT ACGGGGTCTG ACGCTCAGTG
                                                                3720

GAACGAAAAC TCACGTTAAG GGATTTTGGT CATGAGATTA TCAAAAGGA TCTTCACCTA
                                                                3780

GATCCTTTTA AATTAAAAAT GAAGTTTTAA ATCAATCTAA AGTATATATG AGTAAACTTG
                                                                3840

GTCTGACAGT TACCAATGCT TAATCAGTGA GGCACCTATC TCAGCGATCT GTCTATTTCG
                                                                3900

TTCATCCATA GTTGCCTGAC TCCCCGTCGT GTAGATAACT ACGATACGGG AGGGCTTACC
                                                                3960

ATCTGGCCCC AGTGCTGCAA TGATACCGCG AGACCCACGC TCACCGGCTC CAGATTTATC
                                                                4020

AGCAATAAAC CAGCCAGCCG GAAGGGCCGA GCGCAGAAGT GGTCCTGCAA CTTTATCCGC
                                                                4080
```

FIGURE 5E

```
CTCCATCCAG TCTATTAATT GTTGCCGGGA AGCTAGAGTA AGTAGTTCGC CAGTTAATAG
                                                              4140

TTTGCGCAAC GTTGTTGCCA TTGCTACAGG CATCGTGGTG TCACGCTCGT CGTTTGGTAT
                                                              4200

GGCTTCATTC AGCTCCGGTT CCCAACGATC AAGGCGAGTT ACATGATCCC CCATGTTGTG
                                                              4260

CAAAAAGCG GTTAGCTCCT TCGGTCCTCC GATCGTTGTC AGAAGTAAGT TGGCCGCAGT
                                                              4320

GTTATCACTC ATGGTTATGG CAGCACTGCA TAATTCTCTT ACTGTCATGC CATCCGTAAG
                                                              4380

ATGCTTTTCT GTGACTGGTG AGTACTCAAC CAAGTCATTC TGAGAATAGT GTATGCGGCG
                                                              4440

ACCGAGTTGC TCTTGCCCGG CGTCAATACG GGATAATACC GCGCCACATA GCAGAACTTT
                                                              4500

AAAAGTGCTC ATCATTGGAA AACGTTCTTC GGGGCGAAAA CTCTCAAGGA TCTTACCGCT
                                                              4560

GTTGAGATCC AGTTCGATGT AACCCACTCG TGCACCCAAC TGATCTTCAG CATCTTTTAC
                                                              4620

TTTCACCAGC GTTTCTGGGT GAGCAAAAAC AGGAAGGCAA AATGCCGCAA AAAAGGGAAT
                                                              4680

AAGGGCGACA CGGAAATGTT GAATACTCAT ACTCTTCCTT TTTCAATATT ATTGAAGCAT
                                                              4740

TTATCAGGGT TATTGTCTCA TGAGCGGATA CATATTTGAA TGTATTTAGA AAAATAAACA
                                                              4800

AATAGGGGTT CCGCGCACAT TTCCCCGAAA AGTGCCACCT GACGTCTAAG AAACCATTAT
                                                              4860

TATCATGACA TTAACCTATA AAAATAGGCG TATCACGAGG CCCTTTCGTC
                                                    4910
```

HYBRID ADENOVIRUS-AAV VIRUS AND METHODS OF USE THEREOF

CROSS-REFERENCE TO RELATED APPLICATIONS

This is a continuation of U.S. patent application Ser. No. 08/836,087, filed Aug. 25, 1997, now U.S. Pat. No. 5,871,982, which was filed pursuant to 35 USC 371 as the national phase of PCT/US95/14018, filed Oct. 25, 1994, which claims the priority of U.S. patent application Ser. No. 08/331,384, filed Oct. 28, 1994, now U.S. Pat. No. 5,856,152.

This invention was supported by the National Institute of Health Grant No. P30 DK 47757. The United States government has rights in this invention.

FIELD OF THE INVENTION

The present invention relates to the field of vectors useful in somatic gene therapy and the production thereof.

BACKGROUND OF THE INVENTION

Recombinant adenoviruses are capable of providing extremely high levels of transgene delivery to virtually all cell types, regardless of the mitotic state. High titers ($10^{13}$ plaque forming units/ml) of recombinant virus can be easily generated in 293 cells (the adenovirus equivalent to retrovirus packaging cell lines) and cryo-stored for extended periods without appreciable losses.

The primary limitation of this virus as a vector resides in the complexity of the adenovirus genome. A human adenovirus is comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis [see, e.g., Horwitz, Virology, 2d edit., ed. B. N. Fields, Raven Press, Ltd. New York (1990)].

A human adenovirus undergoes a highly regulated program during its normal viral life cycle [Y. Yang et al, *Proc. Natl. Acad. Sci. USA*, 91:4407–4411 (1994)]. Virions are interralized by receptor-mediated endocytosis and transported to the nucleus where the immediate early genes, E1a and E1b, are expressed. Because these early gene products regulate expression of a variety of host genes (which prime the cell for virus production) and are central to the cascade activation of early delayed genes (e.g. E2, E3, and E4) followed by late genes (e.g. L1–5), first generation recombinant adenoviruses for gene therapy focused on the removal of the E1 domain. This strategy was successful in rendering the vectors replication defective, however, in vivo studies revealed transgene expression was transient and invariably associated with the development of severe inflammation at the site of vector targeting [S. Ishibashi et al, *J. Clin. Invest.*, 93:1885–1893 (1994); J. M. Wilson et al, *Proc. Natl. Acad. Sci. USA*, 85:4421–4424 (1988); J. M. Wilson et al, *Clin. Bio.*, 3:21–26 (1991); M. Grossman et al, *Som. Cell. and Mol. Gen.*, 17:601–607 (1991)].

Adeno-associated viruses (AAV) have also been employed as vectors. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene [B. J. Carter, in "Handbook of Parvoviruses", ed., P. Tijsser, CRC Press, pp.155–168 (1990)]. It has been shown that the ITRs represent the minimal sequence required for replication, rescue, packaging, and integration of the AAV genome.

The AAV life cycle is biphasic, composed of both latent and lytic episodes. During a latent infection, AAV virions enter a cell as an encapsidated ssDNA, and shortly thereafter are delivered to the nucleus where the AAV DNA stably integrates into a host chromosome without the apparent need for host cell division. In the absence of helper virus, the integrated ss DNA AAV genome remains latent but capable of being activated and rescued. The lytic phase of the life cycle begins when a cell harboring an AAV provirus is challenged with a secondary infection by a herpesvirus or adenovirus which encodes helper functions that are recruited by AAV to aid in its excision from host chromatin [B. J. Carter, cited above]. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ss DNA genomes following cell lysis.

Progress towards establishing AAV as a transducing vector for gene therapy has been slow for a variety of reasons. While the ability of AAV to integrate in quiescent cells is important in terms of long term expression of a potential transducing gene, the tendency of the integrated provirus to preferentially target only specific sites in chromosome 19 reduces its usefulness. Additionally, difficulties surround large-scale production of replication defective recombinants. In contrast to the production of recombinant retrovirus or adenovirus, the only widely recognized means for manufacturing transducing AAV virions entails co-transfection with two different, yet complementing plasmids. One of these contains the therapeutic or reporter minigene sandwiched between the two cis acting AAV ITRs. The AAV components that are needed for rescue and subsequent packaging of progeny recombinant genomes are provided in trans by a second plasmid encoding the viral open reading frames for rep and cap proteins. The cells targeted for transfection must also be infected with adenovirus thus providing the necessary helper functions. Because the yield of recombinant AAV is dependent on the number of cells that are transfected with the cis and trans-acting plasmids, it is desirable to use a transfection protocol with high efficiency. For large-scale production of high titer virus, however, previously employed high efficiency calcium phosphate and liposome systems are cumbersome and subject to inconsistencies.

There remains a need in the art for the development of vectors which overcome the disadvantages of the known vector systems.

SUMMARY OF THE INVENTION

In one aspect, the present invention provides a unique recombinant hybrid adenovirus/AAV virus, which comprises an adenovirus capsid containing selected portions of an adenovirus sequence, 5' and 3' AAV ITR sequences which flank a selected transgene under the control of a selected promoter and other conventional vector regulatory components. This hybrid virus is characterized by high titer transgene delivery to a host cell and the ability to stably integrate the transgene into the host cell chromosome in the presence of the rep gene. In one embodiment, the transgene is a reporter gene. Another embodiment of the hybrid virus contains a therapeutic transgene. In a preferred embodiment, the hybrid virus has associated therewith a polycation sequence and the AAV rep gene. This construct is termed the hybrid virus conjugate or trans-infection particle.

In another aspect, the present invention provides a hybrid vector construct for use in producing the hybrid virus or viral particle described above. This hybrid vector comprises selected portions of an adenovirus sequence, 5' and 3' AAV ITR sequences which flank a selected transgene under the control of a selected promoter and other conventional vector regulatory components.

In another aspect, the invention provides a composition comprising a hybrid viral particle for use in delivering a selected gene to a host cell. Such a composition may be employed to deliver a therapeutic gene to a targeted host cell to treat or correct a genetically associated disorder or disease.

In yet another aspect, the present invention provides a method for producing the hybrid virus by transfecting a suitable packaging cell line with the hybrid vector construct of this invention. In another embodiment the method involves co-transfecting a cell line (either a packaging cell line or a non-packaging cell line) with a hybrid vector construct and a suitable helper virus.

In a further aspect, the present invention provides a method for producing large quantities of recombinant AAV particles with high efficiency by employing the above methods, employing the hybrid vector construct of this invention and collecting the rAAV particles from a packaging cell line transfected with the vector.

Other aspects and advantages of the present invention are described further in the following detailed description of the preferred embodiments thereof.

BRIEF DESCRIPTION OF THE DRAWINGS

FIG. 1A is a schematic diagram of a vector construct pAd.AV.CMVLacZ [SEQ ID NO: 1], which contains (from the top in clockwise order) adenovirus sequence map units 0–1 (clear bar); the 5' AAV ITR (solid bar); a CMV immediate early enhancer/promoter (hatched arrow), an SV40 intron (clear bar), an E. coli beta-galactosidase cDNA (LacZ) (hatched line), an SV40 polyadenylation signal (clear bar), a 3' AAV ITR (solid bar), adenovirus sequence from map units 9–16 (clear bar), and a portion of a pBR322 derivative plasmid (thin solid line). Restriction endonuclease enzymes are identified by their conventional designations; and the location of each restriction enzyme is identification by the nucleotide number in parentheses to the right of the enzyme designation.

FIG. 1B is a schematic drawing demonstrating linearization of pAd.AV.CMVLacZ [SEQ ID NO: 1] by digestion with restriction enzyme NheI and a linear arrangement of a ClaI digested adenovirus type 5 with deletions from mu 0–1. The area where homologous recombination will occur (between m.u. 9–16) in both the plasmid and adenovirus sequences is indicated by crossed lines.

FIG. 1C is a schematic drawing which demonstrates the hybrid virus Ad.AV.CMVLacZ after co-transfection of the linearized pAd.AV.CMVLacZ [SEQ ID NO: 1] and adenovirus into 293 cells followed by intracellular homologous recombination.

FIG. 2A–2K report the top DNA strand of the double-strand plasmid pAd.AV.CMVLacZ [SEQ ID NO: 1] (the complementary strand can be readily derived by one of skill in the art). With reference to SEQ ID NO: 1, nucleotides 1–365 are adenovirus type 5 sequences; the 5' AAV ITR sequence spans nucleotides 366–538; the CMV promoter/enhancer spans nucleotides 563–1157; the SV-40 intron spans nucleotides 1158–1179; the LacZ gene spans nucleotides 1356–4827; the SV-40 poly A sequence spans nucleotides 4839–5037; the 3' AAV ITR spans nucleotides 5053 to 5221; nucleotides 5221 to about 8100 are adenovirus type 5 sequences. The remaining sequences are non-specific/plasmid sequences.

FIGS. 5A–5E report nucleotides 1–4910 of the top DNA strand of the double-strand plasmid pRep78/52 [SEQ ID NO: 2] (the complementary strand can be readily derived by one of skill in the art).

DETAILED DESCRIPTION OF THE INVENTION

Figure 3:
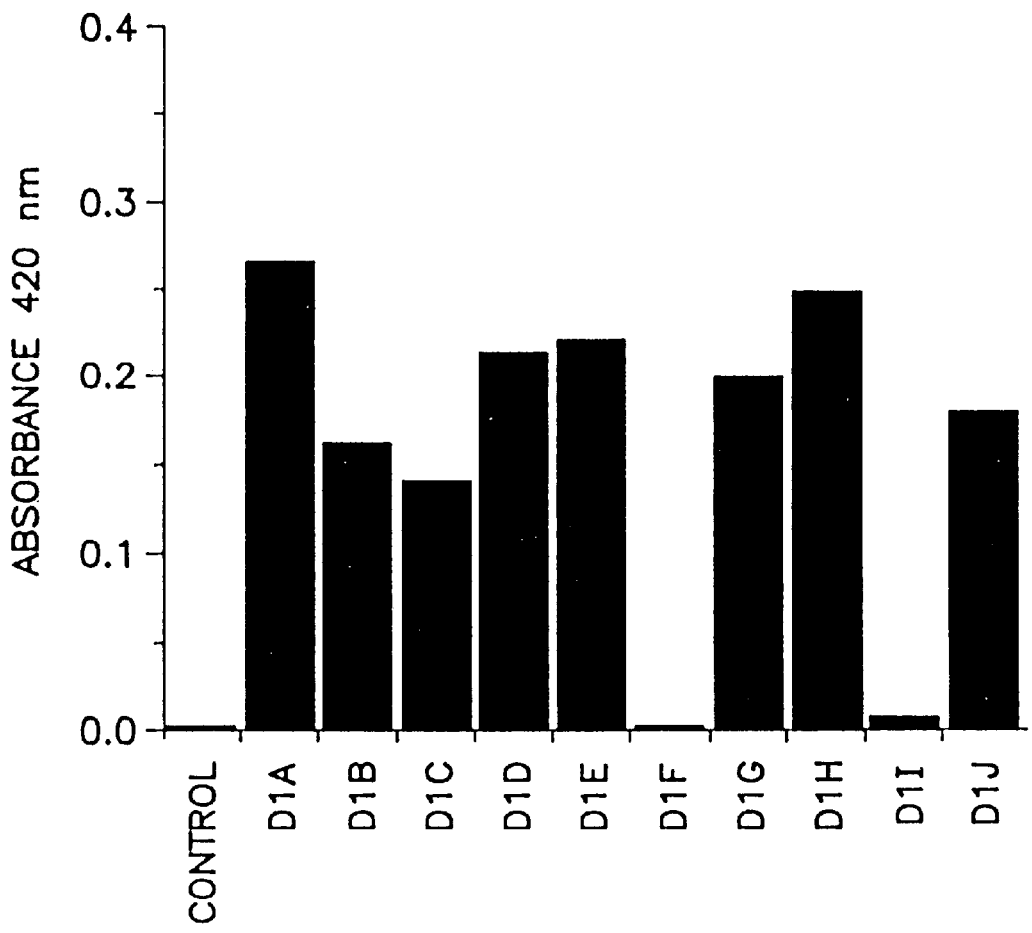
FIG. 3 is a bar graph plotting u.v. absorbance at 420 nm of the beta-galactosidase blue color for a control and ten putative positive clones (D1A through D1J) of 293 cells transfected with the recombinant hybrid Ad.AV.CMVLacZ. Eight of the clones expressed high levels of enzyme.
Figure 4:
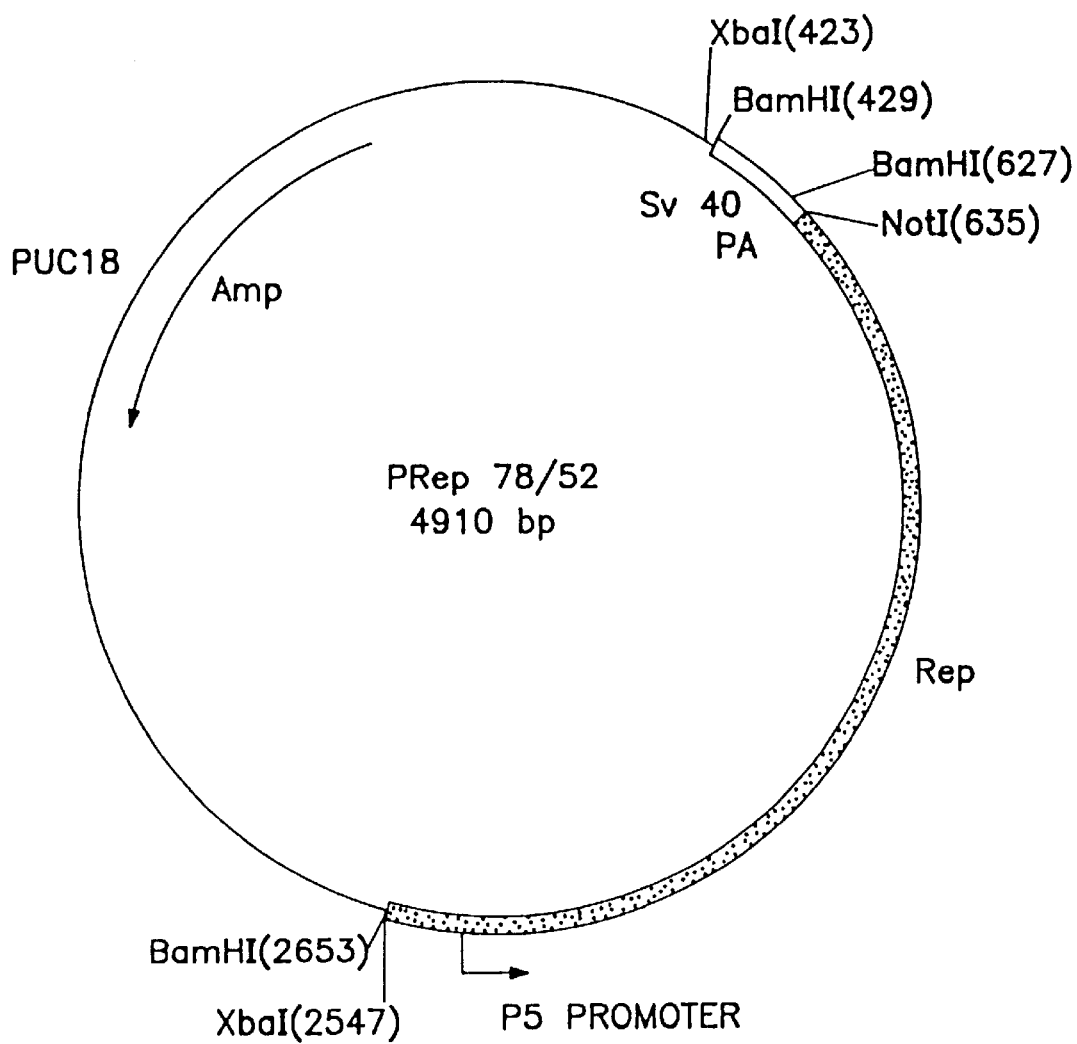
FIG. 4 is a schematic diagram of pRep78/52 [SEQ ID NO: 2]. This plasmid includes an AAV P5 promoter, Rep78, Rep52 and a poly-A sequence in a pUC18 plasmid background.
Figure 6:
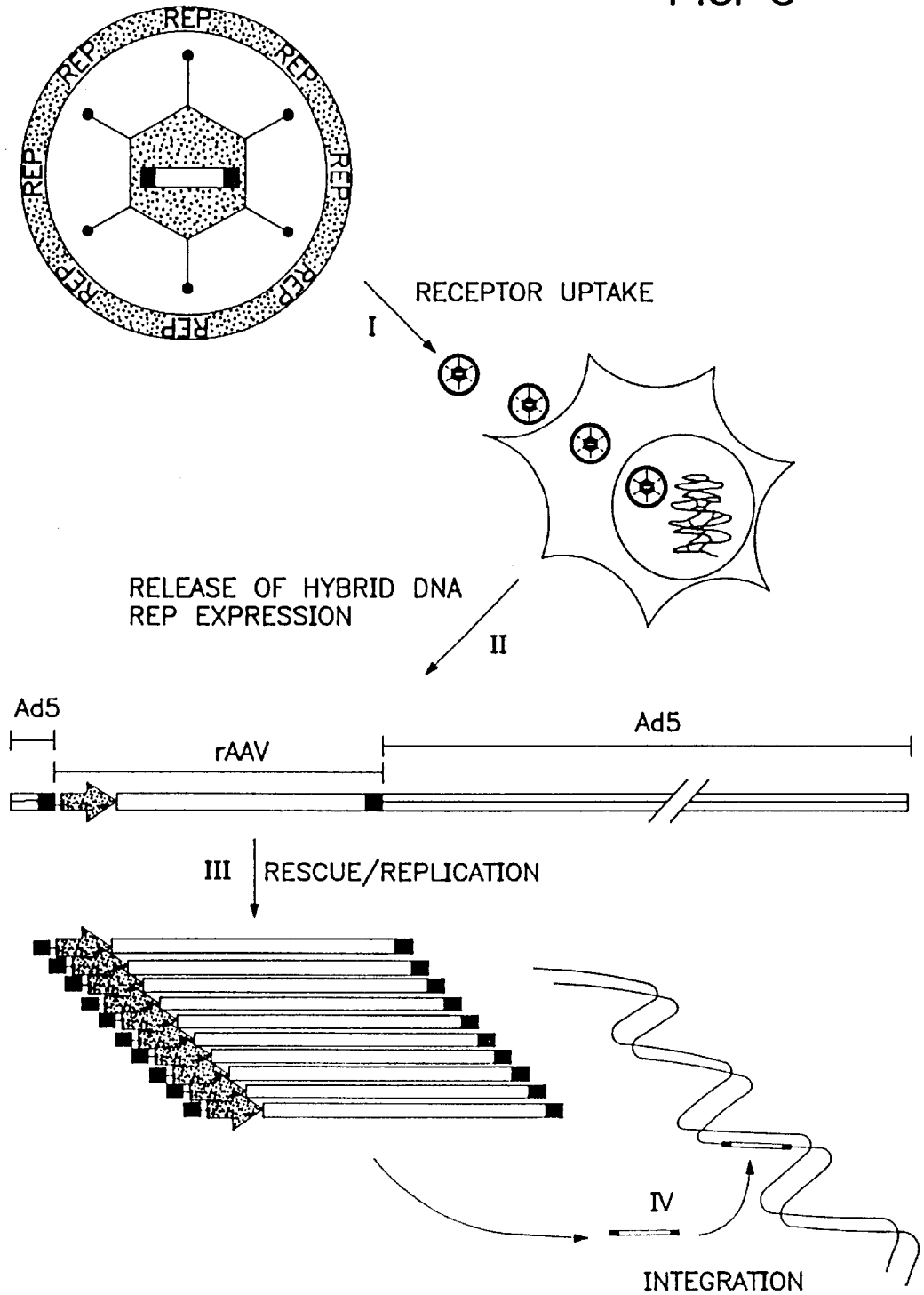
FIG. 6 is a flow diagram of the construction of a trans-infection particle formed by a hybrid virus, a poly-L-lysine sequence and attached AAV rep-containing plasmid.

The present invention provides a unique gene transfer vehicle which overcomes many of the limitations of prior art viral vectors. This engineered hybrid virus contains selected adenovirus domains and selected AAV domains as well as a selected transgene and regulatory elements in a viral capsid. This novel hybrid virus solves the problems observed with other, conventional gene therapy viruses, because it is characterized by the ability to provide extremely high levels of transgene delivery to virtually all cell types (conferred by its adenovirus sequence) and the ability to provide stable long-term transgene integration into the host cell (conferred by its AAV sequences). The adenovirus-AAV hybrid virus of this invention has utility both as a novel gene transfer vehicle and as a reagent in a method for large-scale recombinant AAV production.

In a preferred embodiment, a trans-infection particle or hybrid virus conjugate composed of the hybrid Ad/AAV virus conjugated to a rep expression plasmid via a poly-lysine bridge is provided. This trans-infection particle is advantageous because the adenovirus carrier can be grown to titers sufficient for high MOI infections of a large number of cells, the adenoviral genome is efficiently transported to the nucleus in nondividing cells as a complex facilitating transduction into mitotically quiescent cells, and incorporation of the rep plasmid into the trans-infection particle provides high but transient expression of rep that is necessary for both rescue of rAAV DNA and efficient and site-specific integration.

I. Construction of the Hybrid Vector and Virus

A. The Adenovirus Component of the Vector and Virus

The hybrid virus of this invention uses adenovirus nucleic acid sequences as a shuttle to deliver a recombinant AAV/transgene genome to a target cell. The DNA sequences of a number of adenovirus types, including type AdS, are available from Genbank. The adenovirus sequences may be obtained from any known adenovirus type, including the presently identified 41 human types [Horwitz et al, cited above]. Similarly adenoviruses known to infect other animals may also be employed in the vector constructs of this invention. The selection of the adenovirus type is not anticipated to limit the following invention. A variety of adenovirus strains are available from the American Type Culture Collection, Rockville, Maryland, or available by request from a variety of commercial and institutional sources. In the following exemplary embodiment an adenovirus, type 5 (Ad5) is used for convenience.

The adenovirus nucleic acid sequences employed in the hybrid vector of this invention can range from a minimum sequence amount, which requires the use of a helper virus to produce the hybrid virus particle, to only selected deletions of adenovirus genes, which deleted gene products can be supplied in the hybrid viral production process by a selected packaging cell. Specifically, at a minimum, the adenovirus nucleic acid sequences employed in the pAdA shuttle vector of this invention are adenovirus genomic sequences from which all viral genes are deleted and which contain only those adenovirus sequences required for packaging adenoviral genomic DNA into a preformed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. According to this invention, the entire adenovirus 5' sequence containing the 5' ITR and packaging/enhancer region can be employed as the 5' adenovirus sequence in the hybrid virus. This left terminal (5') sequence of the Ad5 genome useful in this invention spans bp 1 to about 360 of the conventional adenovirus genome, also referred to as map units 0–1 of the viral genome, and generally is from about 353 to about 360 nucleotides in length. This sequence includes the 5' ITR (bp 1–103 of the adenovirus genome); and the packaging/enhancer domain (bp 194–358 of the adenovirus genome). Preferably, this native adenovirus 5' region is employed in the hybrid virus and vector in unmodified form. Alternatively, corresponding sequences from other adenovirus types may be substituted. These Ad sequences may be modified to contain desired deletions, substitutions, or mutations, provided that the desired function is not eliminated.

The 3' adenovirus sequences of the hybrid virus include the right terminal (3') ITR sequence of the adenoviral genome spanning about bp 35,353-end of the adenovirus genome, or map units ~98.4–100. This sequence is generally about 580 nucleotide in length. This entire sequence is desirably employed as the 3' sequence of a hybrid virus. Preferably, the native adenovirus 3' region is employed in the hybrid virus in unmodified form. However, as described above with respect to the 5' sequences, some modifications to these sequences which do not adversely effect their biological function may be acceptable. As described below, when these 5' and 3' adenovirus sequences are employed in the hybrid vector, a helper adenovirus which supplies all other essential genes for viral formation alone or with a packaging cell line is required in the production of the hybrid virus or viral particle.

Alternative embodiments of the hybrid virus employ adenovirus sequences in addition to the minimum sequences, but which contain deletions of all or portions of adenovirus genes. For example, the adenovirus immediate early gene E1a (which spans mu 1.3 to 4.5) and delayed early gene E1b(which spans mu 4.6 to 11.2) should be deleted from the adenovirus sequence which forms a part of the hybrid vector construct and virus. Alternatively, if these sequences are not completely eliminated, at least a sufficient portion of the E1a and E1bsequences must be deleted so as to render the virus replication defective. These deletions, whether complete or partial, which eliminate the biological function of the gene are termed "functional deletions" herein.

Additionally, all or a portion of the adenovirus delayed early gene E3 (which spans mu 76.6 to 86.2) may be eliminated from the adenovirus sequence which forms a part of the hybrid virus. The function of E3 is irrelevant to the function and production of the hybrid virus.

All or a portion of the adenovirus delayed early gene E2a (which spans mu 67.9 to 61.5) may be eliminated from the hybrid virus. It is also anticipated that portions of the other delayed early genes E2b (which spans mu 29 to 14.2) and E4 (which spans mu 96.8 to 91.3) may also be eliminated from the hybrid virus and from the vector.

Deletions may also be made in any of the late genes L1 through L5, which span mu 16.45 to 99 of the adenovirus genome. Similarly, deletions may be useful in the intermediate genes IX which maps between mu 9.8 and 11.2 and $IVa_2$ which maps between 16.1 to 11.1. Other deletions may occur in the other structural or non-structural adenovirus.

The above discussed deletions may occur individually, i.e., an adenovirus sequence for use in the present invention may contain deletions of E1 only. Alternatively, deletions of entire genes or portions effective to destroy their biological activity may occur in any combination. For example, in one exemplary hybrid vector, the adenovirus sequence may contain deletions of the E1 genes and the E3 gene, or of the E1, E2a and E3 genes, or of the E1 and E4 genes, or of E1, E2a and E4 genes, with or without deletion of E3, and so on.

The more deletions in the adenovirus sequence up to the minimum sequences identified above that characterize the hybrid virus, the larger the sequence(s) of the other below-described components to be inserted in the hybrid vector. As described above for the minimum adenovirus sequences, those gene sequences not present in the adenovirus portion of the hybrid virus must be supplied by either a packaging cell line and/or a helper adenovirus to generate the hybrid virus.

In an exemplary hybrid virus of this invention which is described below and in Example 1, the adenovirus genomic sequences present are from mu 0 to 1, mu 9 to 78.3 and mu 86 to 100 (deleted sequences eliminate the E1a and E1genes and a portion of the E3 gene). From the foregoing information, it is expected that one of skill in the art may construct hybrid vectors and viruses containing more or less of the adenovirus gene sequence.

The portions of the adenovirus genome in the hybrid virus permit high production titers of the virus to be produced, often greater than $1\times10^{13}$ pfu/ml. This is in stark contrast to the low titers ($1\times10^6$ pfu/ml) that have been found for recombinant AAV.

B. The AAV Components of the Vector and Virus

Also part of the hybrid vectors and viruses of this invention are sequences of an adeno-associated virus. The AAV sequences useful in the hybrid vector are the viral sequences from which the rep and cap polypeptide encoding sequences are deleted. More specifically, the AAV sequences employed are the cis-acting 5' and 3' inverted terminal repeat (ITR) sequences [See, e.g., B. J. Carter, in "Handbook of Parvoviruses", ed., P. Tijsser, CRC Press, pp.155–168 (1990)]. As stated above, the ITR sequences are about 143 bp in length. Substantially the entire sequences encoding the ITRs are used in the vectors, although some degree of minor modification of these sequences is expected to be permissible for this use. See, e.g., WO 93/24641, published Dec. 9, 1993. The ability to modify these ITR sequences is within the skill of the art. For suitable techniques, see, e.g., texts such as Sambrook et al, "Molecular Cloning. A Laboratory Manual.", 2d edit., Cold Spring Harbor Laboratory, New York (1989).

The AAV ITR sequences may be obtained from any known AAV, including presently identified human AAV types. similarly, AAVs known to infect other animals may also be employed in the vector constructs of this invention. The selection of the AAV is not anticipated to limit the following invention. A variety of AAV strains, types 1–4, are available from the American Type Culture Collection or available by request from a variety of commercial and institutional sources. In the following exemplary embodiment an AAV-2 is used for convenience.

In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a /E1genes of the adenovirus, i.e., after map unit 1. Alternatively, the AAV sequences may be inserted at an E3 deletion, E2a deletion, and so on. If only the adenovirus 5' ITR/packaging sequences and 3' ITR sequences are used in the hybrid virus, the AAV sequences are inserted between them.

C. The Transgene Component of the Hybrid Vector and Virus

The transgene sequence of the vector and recombinant virus is a nucleic acid sequence or reverse transcript thereof, heterologous to the adenovirus sequence, which encodes a polypeptide or protein of interest. The transgene is operatively linked to regulatory components in a manner which permits transgene transcription.

The composition of the transgene sequence will depend upon the use to which the resulting hybrid vector will be put. For example, one type of transgene sequence includes a reporter sequence, which upon expression produces a detectable signal. Such reporter sequences include without limitation an E. coli beta-galactosidase (LacZ) cDNA, an alkaline phosphatase gene and a green fluorescent protein gene. These sequences, when associated with regulatory elements which drive their expression, provide signals detectable by conventional means, e.g., ultraviolet wavelength absorbance, visible color change, etc.

Another type of transgene sequence includes a therapeutic gene which expresses a desired gene product in a host cell. These therapeutic genes or nucleic acid sequences typically encode products for administration and expression in a patient in vivo or ex vivo to replace or correct an inherited or non-inherited genetic defect or treat an epigenetic disorder or disease. Such therapeutic genes which are desirable for the performance of gene therapy include, without limitation, a normal cystic fibrosis transmembrane regulator (CFTR) gene, a low density lipoprotein (LDL) gene, and a number of genes which may be readily selected by one of skill in the art. The selection of the transgene is not considered to be a limitation of this invention, as such selection is within the knowledge of those skilled in the art.

D. Regulatory Elements of the Hybrid Vector

In addition to the major elements identified above for the hybrid vector, i.e., the adenovirus sequences, AAV sequences and the transgene, the vector also includes conventional regulatory elements necessary to drive expression of the transgene in a cell transfected with the hybrid vector. Thus the vector contains a selected promoter which is linked to the transgene and located, with the transgene, between the AAV ITR sequences of the vector.

Selection of the promoter is a routine matter and is not a limitation of the hybrid vector itself. Useful promoters may be constitutive promoters or regulated (inducible) promoters, which will enable control of the amount of the transgene to be expressed. For example, a desirable promoter is that of the cytomegalovirus immediate early promoter/enhancer [see, e.g., Boshart et al, Cell, 41:521–530 (1985)]. Other desirable promoters include, without limitation, the Rous sarcoma virus LTR promoter/enhancer and the chicken β-actin promoter. Still other promoter/enhancer sequences may be selected by one of skill in the art.

The vectors will also desirably contain nucleic acid sequences heterologous to the adenovirus sequences including sequences providing signals required for efficient polyadenylation of the transcript and introns with functional splice donor and acceptor sites. A common poly-A sequence which is employed in the exemplary vectors of this invention is that derived from the papovavirus SV-40. The poly-A sequence generally is inserted in the vector following the transgene sequences and before the 3' AAV ITR sequence. A common intron sequence is also derived from SV-40, and is referred to as the SV-40 T intron sequence. A hybrid vector of the present invention may also contain such an intron, desirably located between the promoter/enhancer sequence and the transgene. Selection of these and other common vector elements are conventional and many such sequences are available [see, e.g., Sambrook et al, and references cited therein]. The DNA sequences encoding such regulatory regions are provided in the plasmid sequence of FIG. 2 [SEQ ID NO: 1].

The combination of the transgene, promoter/enhancer, the other regulatory vector elements and the flanking 5' and 3' AAV ITRs are referred to as a "minigene" for ease of reference herein. As above stated, the minigene is located in the site of any selected adenovirus deletion in the hybrid virus. The size of this minigene depends upon the amount and number of adenovirus sequence deletions referred to above. Such a minigene may be about 8 kb in size in the exemplary virus deleted in the E1 and E3 genes, as described in the examples below. Alternatively, if only the minimum adenovirus sequences are employed in the virus, this minigene may be a size up to about 30 kb. Thus, this hybrid vector and vector permit a great deal of latitude in the selection of the various components of the minigene, particularly the transgene, with regard to size. Provided with the teachings of this invention, the design of such a minigene can be made by resort to conventional techniques.

E. Hybrid Vector Assembly and Production of Hybrid Virus

The material from which the sequences used in the hybrid vector, helper viruses, if needed, and recombinant hybrid virus (or viral particle) are derived and the various vector components and sequences employed in the construction of the hybrid vectors of this invention are obtained from commercial or academic sources based on previously published and described materials. These materials may also be obtained from an individual patient or generated and selected using standard recombinant molecular cloning techniques known and practiced by those skilled in the art. Any modification of existing nucleic acid sequences forming the vectors and viruses, including sequence deletions, insertions, and other mutations are also generated using standard techniques.

Assembly of the selected DNA sequences of the adenovirus, the AAV and the reporter genes or therapeutic genes and other vector elements into the hybrid vector and the use of the hybrid vector to produce a hybrid virus utilize conventional techniques, such as described in Example 1. Such techniques include conventional cloning techniques of cDNA such as those described in texts [Sambrook et al, cited above], use of overlapping oligonucleotide sequences of the adenovirus and AAV genomes, polymerase chain reaction, and any suitable method which provides the desired nucleotide sequence. Standard transfection and co-transfection techniques are employed, e.g., $CaPO_4$ transfection techniques using the complementation human embryonic kidney (HEK) 293 cell line (a human kidney cell line containing a functional adenovirus E1a gene which provides a transacting E1a protein). other conventional methods employed in this invention include homologous recombination of the viral genomes, plaquing of viruses in agar overlay, methods of measuring signal generation, and the like.

As described in detail in Example 1 below and with resort to FIG. 1, a unique hybrid virus of this invention is prepared which contains an E1-deleted, partially E3 deleted, adenovirus sequence associated with a single copy of a recombinant AAV having deletions of its rep and cap genes and encoding a selected reporter transgene. Briefly, this exemplary hybrid virus was designed such that the AV.CMVLacZ sequence [SEQ ID NO: 1] (a minigene containing a 5'AAV ITR, a CMV promoter, an SV-40 intron, a LacZ transgene, an SV-40 poly-A sequence and a 3' AAV ITR) was positioned in place of the adenovirus type 5 (Ad5) E1a/E1genes, making the adenovirus vector replication defective.

Because of the limited amount of adenovirus sequence present in the hybrid vectors of this invention, including the pAV.CMVLacZ [SEQ ID NO: 1] above, a packaging cell line or a helper adenovirus or both may be necessary to provide sufficient adenovirus gene sequences necessary for a productive viral infection to generate the hybrid virus.

Helper viruses useful in this invention contain selected adenovirus gene sequences not present in the hybrid vector construct or expressed by the cell line in which the hybrid vector is transfected. Optionally, such a helper virus may contain a second reporter minigene which enables separation of the resulting hybrid virus and the helper virus upon purification. The construction of desirable helper viruses is within the skill of the art.

As one example, if the cell line employed to produce the recombinant virus is not a packaging cell line, and the hybrid vector contains only the minimum adenovirus sequences identified above, the helper virus may be a wild type Ad virus. Thus, the helper virus supplies the necessary adenovirus early genes E1, E2a, E4 and all remaining late, intermediate, structural and non-structural genes of the adenovirus genome. However, if, in this situation, the packaging cell line is 293, which supplies the E1 proteins, the helper virus need not contain the E1 gene.

In another embodiment, when the hybrid construct is rendered replication defective by a functional deletion in E1 but contains no other deletions in Ad genes necessary for production of an infective viral particle, and the 293 cell line is employed, no helper virus is necessary for production of the hybrid virus. Additionally, all or a portion of the adenovirus delayed early gene E3 (which spans mu 76.6 to 86.2) may be eliminated from the helper virus useful in this invention because this gene product is not necessary for the formation of a functioning hybrid virus particle.

It should be noted that one of skill in the art may design other helper viruses or develop other packaging cell lines to complement the adenovirus deletions in the vector construct and enable production of the hybrid virus particle, given this information. Therefore, this invention is not limited by the use or description of any particular helper virus or packaging cell line.

Thus, as described in FIGS. 1A through 1C, the circular plasmid pAd.AV.CMVLacZ [SEQ ID NO: 1] (containing the minigene and only adenovirus sequences from map unit 0 to 1 and 9 to 16) was digested and co-transfected with a selected Ad5 helper virus (containing adenovirus sequences 9 to 78.4 and 86 to 100) into 293 cells. Thus, the packaging cell line provides the E1 proteins and the helper virus provides all necessary adenovirus gene sequences subsequent to map unit 16. Homologous recombination occurs between the helper virus and the hybrid vector, resulting in the hybrid viral particle. Growth of this hybrid viral particle in 293 cells has been closely monitored for greater than 20 rounds of amplification with no indication of genome instability. Rescue and integration of the transgene from the hybrid virus into a host cell and further modifications of the vector are described below. The resulting hybrid virus Ad.AV.CMVLacZ combines the high titer potential of adenovirus with the integrating biology associated with AAV latency.

G. Hybrid Virus Polycation Conjugates

Rep expression is required for rescue of the rAAV genome to occur. A preferred approach is to synthetically incorporate a plasmid permitting expression of rep into the hybrid particle. To do so, the hybrid viruses described above are further modified by resort to adenovirus-polylysine conjugate technology. See, e.g., Wu et al, *J. Biol. Chem.*, 264:16985–16987 (1989); and K. J. Fisher and J. M. Wilson, *Biochem. J.*, 299: 49 (Apr. 1, 1994), incorporated herein by reference. Using this technology, a hybrid virus as described above is modified by the addition of a poly-cation sequence distributed around the capsid of the hybrid viral particle. Preferably, the poly-cation is poly-lysine, which attaches around the negatively-charged virus to form an external positive charge. A plasmid containing the AAV rep gene (or a functional portion thereof) under the control of a suitable promoter is then complexed directly to the hybrid capsid, resulting in a single viral particle containing the hybrid virus and an AAV rep gene. The negatively charged plasmid DNA binds with high affinity to the positively charged polylysine. Essentially the techniques employed in constructing this hybrid virus conjugate or trans-infection particle are as described in detail in Example 3 below.

An alternative embodiment of the hybrid vector and resulting viral particle is provided by altering the rep containing plasmid to also contain an AAV cap gene. This embodiment of the hybrid vector when in a host cell is thus able to produce a recombinant AAV particle, as discussed in more detail below.

The plasmids employed in these embodiments contain conventional plasmid sequences, which place a selected AAV sequence, i.e., rep and/or cap gene sequences, under the control of a selected promoter. In the example provided below, the exemplary plasmid is pRep78/52 [SEQ ID NO: 2], a trans-acting plasmid containing the AAV sequences that encode rep 78 kD and 52 kD proteins under the control of the AAV P5 promoter. The plasmid also contains an SV40 polyadenylation signal. The DNA sequence of this plasmid is provided in FIG. 8 [SEQ ID NO: 2].

In a similar manner and with resort to plasmid and vector sequences known to the art, analogous plasmids may be designed using both rep and cap genes, and different constitutive or regulated promoters, optional poly-A sequences and introns.

The availability of materials to make these modified hybrid vectors and viruses and the AAV rep and/or cap containing vectors and the techniques involved in the assembly of the hybrid vector and rep and/or cap containing plasmids are conventional as described above. The assembly techniques for the trans-infection particle employ the techniques described above for the hybrid vector and the techniques of Wu et al and Fisher et al, cited above. The use of this trans-infection particle including rescue and integration of the transgene into the host cell is described below.

II. Function of the Hybrid Virus

A. The Hybrid Virus Infects a Target Cell

Once the hybrid virus or trans-infection particle is constructed as discussed above, it is targeted to, and taken up by, a selected target cell. The selection of the target cell also depends upon the use of the hybrid virus, i.e., whether or not the transgene is to be replicated in vitro for production of a recombinant AAV particle, or ex vivo for production into a desired cell type for redelivery into a patient, or in vivo for delivery to a particular cell type or tissue. Target cells may therefor be any mammalian cell (preferably a human cell). For example, in in vivo use, the hybrid virus can target to any cell type normally infected by adenovirus, depending upon the route of administration, i.e., it can target, without limitation, neurons, hepatocytes, epithelial cells and the like. Uptake of the hybrid virus by the cell is caused by the infective ability contributed to the vector by the adenovirus and AAV sequences.

B. The Transgene is Rescued.

Once the hybrid virus or trans-infection particle is taken up by a cell, the AAV ITR flanked transgene must be rescued from the parental adenovirus backbone. Rescue of the transgene is dependent upon supplying the infected cell with an AAV rep gene. Thus, efficacy of the hybrid virus can be measured in terms of rep mediated rescue of rAAV from the parental adenovirus template.

The rep genes can be supplied to the hybrid virus by several methods. One embodiment for providing rep proteins in trans was demonstrated with the exemplary hybrid virus Ad.AV.CMVLacZ by transfecting into the target monolayer of cells previously infected with the hybrid vector, a liposome enveloped plasmid pRep78/52 [SEQ ID NO: 2] containing the genes encoding the AAV rep 78 kDa and 52 kDa proteins under the control of the AAV Ppromoter. Rescue and amplification of a double-stranded AAV monomer and a double-stranded AAV dimer, each containing the LacZ transgene described above, was observed in 293 cells. This is described in detail in Example 2.

The production of rep in trans can be modulated by the choice of promoter in the rep containing plasmid. If high levels of rep expression are important early for rescue of the recombinant AAV domain, a heterologous (non-adenovirus, non-AAV) promoter may be employed to drive expression of rep and eliminate the need for E1 proteins. Alternatively, the low levels of rep expression from P5 that occur in the absence of adenovirus E1 proteins may be sufficient to initiate rescue and optimal to drive integration of the recombinant AAV genome in a selected use.

More preferably for in vivo use, the AAV rep gene may also be delivered as part of the hybrid virus. One embodiment of this single particle concept is the polycation conjugated hybrid virus (see FIG. 7). Infection of this trans-infection particle is accomplished in the same manner and with regard to the same target cells as identified above. The polylysine conjugate of the hybrid virus onto which was directly complexed a plasmid that encoded the rep 78 and 52 proteins, combines all of the functional components into a single particle structure. Thus, the trans-infection particle permits delivery of a single particle to the cell, which is considerably more desirable for therapeutic use. Similar experiments to demonstrate rescue of the transgene from the hybrid conjugate trans-infection particle in 293 cells and in HeLa cells are detailed in Example 4.

In another embodiment, the hybrid virus is modified by cloning the rep CDNA directly into the adenovirus genome portion of the hybrid vector. Because it is known that even residual levels of rep expression can interfere with replication of adenovirus DNA, such incorporation of rep into the hybrid vector itself is anticipated to requires possible mutation of the rep genes to encode only selected domains, and the use of inducible promoters to regulate rep expression, as well as careful placement of the rep genes into the adenovirus sequences of the hybrid vector.

C. Transgene Integrates into Chromosome

Figure 7:
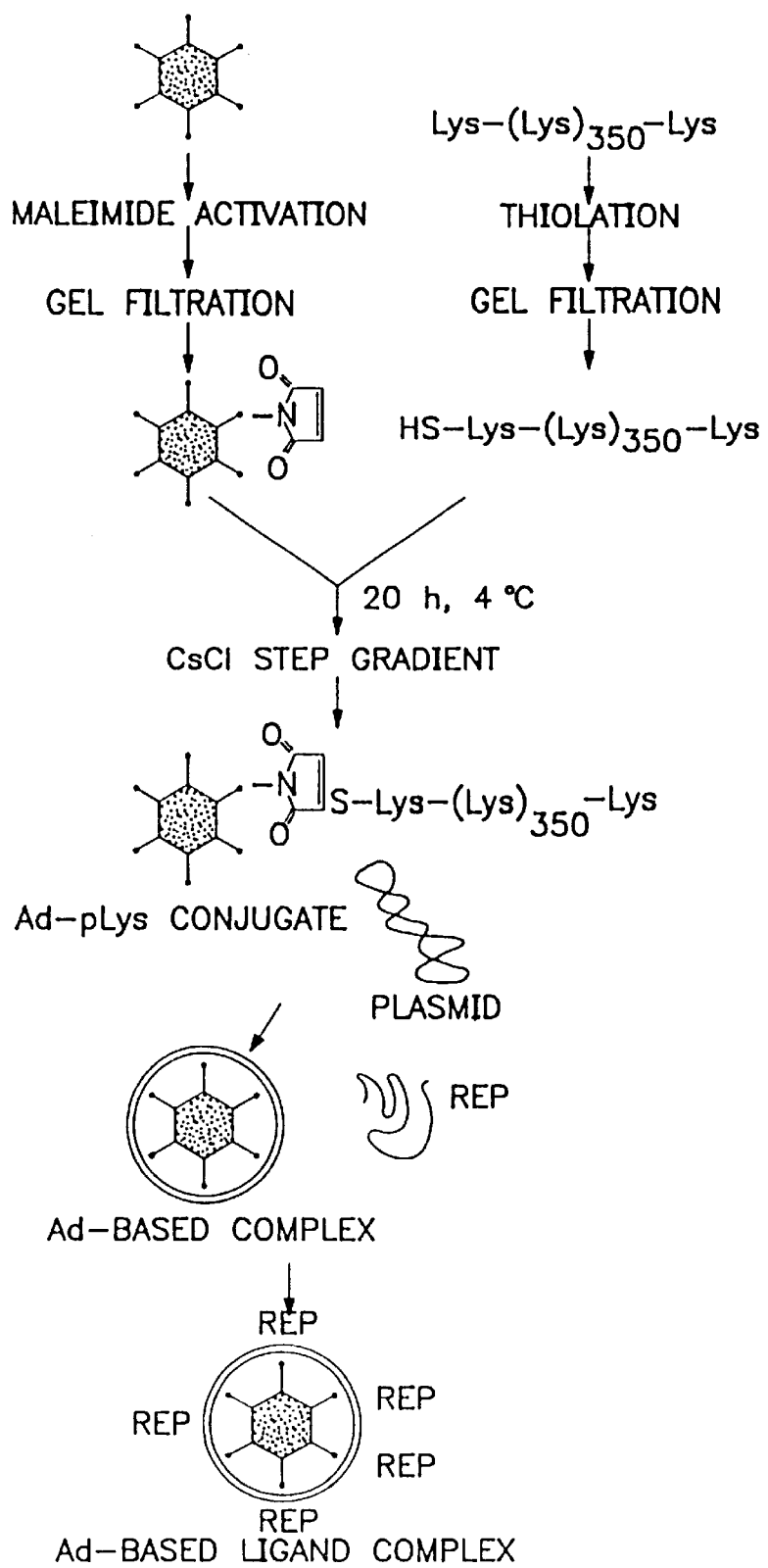
FIG. 7 is a flow diagram of the hybrid virus' life cycle, in which a trans-infection particle enters the cell and is transported to the nucleus. The virus is uncoated and the rep mediates rescue of the inserted gene, which is then integrated into the chromosome of the host cell.

Once uncoupled (rescued) from the genome of the hybrid virus, the recombinant AAV/transgene minigene seeks an integration site in the host chromatin and becomes integrated therein, providing stable expression of the accompanying transgene in the host cell. This aspect of the function of the hybrid virus is important for its use in gene therapy. The AAV/transgene minigene sequence rescued from the hybrid virus achieves provirus status in the target cell, i.e., the final event in the hybrid lifecycle (FIG. 7).

To determine whether the AAV minigene rescued from the hybrid virus achieves provirus status in a target cell, non-E1 expressing HeLa cells were infected with the hybrid vector-poly-Lysine conjugate complexed with pRep78/52 [SEQ ID NO: 2] and passaged until stable colonies of LacZ expressing cells are evident. A duplicate plate of cells was infected with the same conjugate, but instead of being complexed with the pRep78/52 plasmid [SEQ ID NO: 2], carried an irrelevant plasmid. Cells that receive the rep containing hybrid particle produced a greater number of stable LacZ positive colonies than cells infected with the control vector. This indicates multiple rescue and integration events in cells that expressed rep proteins. Confirmation of integration is revealed by characterizing the recombinant AAV genome in the hybrid infected cells and identifying flanking chromosomal sequences (see Example 5).

III. Use of the Hybrid Viruses and Viral Particles in Gene Therapy

The novel hybrid virus and trans-infection particles of this invention provide efficient gene transfer vehicles for somatic gene therapy. These hybrid viruses are prepared to contain a therapeutic gene in place of the LacZ reporter transgene illustrated in the exemplary vector. By use of the hybrid viruses and trans-infection particles containing therapeutic transgenes, these transgenes can be delivered to a patient in vivo or ex vivo to provide for integration of the desired gene into a target cell. Thus, these hybrid viruses and trans-infection particles can be employed to correct genetic deficiencies or defects. Two examples of the generation of gene transfer vehicles for the treatment of cystic fibrosis and familial hypercholesterolemia are described in Examples 6 and 7 below. One of skill in the art can generate any number of other gene transfer vehicles by including a selected transgene for the treatment of other disorders. For example, the trans-infection particles are anticipated to be particularly advantageous in ex vivo gene therapy where transduction and proviral integration in a stem cell is desired, such as in bone marrow directed gene therapy.

The hybrid viruses and trans-infection particles of the present invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The hybrid viruses and trans-infection particles of this invention may be administered in sufficient amounts to transfect the desired cells and provide sufficient levels of integration and expression of the selected transgene to provide a therapeutic benefit without undue adverse or with medically acceptable physiological effects which can be determined by those skilled in the medical arts. Conventional and pharmaceutically acceptable routes of administration include direct delivery to the target organ, tissue or site, intranasal, intravenous, intramuscular, subcutaneous, intradermal, oral and other parental routes of administration. Routes of administration may be combined, if desired.

Dosages of the hybrid virus and/or trans-infection particle will depend primarily on factors such as the condition being treated, the selected gene, the age, weight and health of the patient, and may thus vary among patients. A therapeutically effective human dose of the hybrid viruses or trans-infection particles of the present invention is believed to be in the range of from about 20 to about 50 ml of saline solution containing concentrations of from about $1 \times 10^7$ to $1 \times 10^{10}$ pfu/ml hybrid virus of the present invention. A preferred human dose is about 20 ml saline solution at the above concentrations. The dosage will be adjusted to balance the therapeutic benefit against any side effects. The levels of expression of the selected gene can be monitored to determine the selection, adjustment or frequency of dosage administration.

IV. High Efficiency Production of rAAV

The hybrid viruses and trans-infection particles of this invention have another desirable utility in the production of large quantities of recombinant AAV particles. Due to the complicated current methods for generating AAV, there is only a limited amount of AAV available for use in industrial, medical and academic biotechnology procedures. The vectors and viruses of the present invention provide a convenient and efficient method for generating large quantities of rAAV particles.

According to this aspect of the invention, a trans-infection particle is constructed as described above and in Example 3 and is employed to produce high levels of rAAV as detailed in Example 8, with the possible modifications described in Example 9 below. Briefly, a plasmid is generated that contains both AAV rep and cap genes under the control of a suitable plasmid and is complexed to the poly-lysine exterior of the hybrid virus as described above. This trans-infection particle is then permitted to infect a selected host cell, such as 293 cells. The presence of both rep and cap permit the formation of AAV particles in the cells and generate an AAV virus titer of about 09 virions. In contrast, current methods involving the transfection of multiple plasmids produce only about $10^7$ virion titer.

The rAAV is isolated from the culture by selecting the LacZ-containing blue plaques and purifying them on a cesium chloride gradient.

The benefit of this procedure relates to the fact that the cis AAV element is encoded by the parental adenovirus genome. As a result, the trans plasmid is the only DNA component that is needed for complex formation. The cell is thereby loaded with significantly more copies of the trans-acting rep and cap sequences, resulting in improved efficiency of rescue and packaging.

Numerous comparative studies focusing on the optimal ratio and copy number of the cis and trans plasmids for AAV production indicated that there is a positive correlation between the trans plasmid copy number and yield of recombinant virus. As described in detail in Example 8, the yield of recombinant AV.CMVLacZ virus was increased by 5–10 fold by using the trans-infection particle instead of a standard adenovirus vector.

The primary limitation associated with the production of recombinant AAV using a hybrid virus of this invention relates to difficulties that arise in distinguishing between the two viruses (i.e., adenovirus and AAV) that are produced by the cell. Using the exemplary vectors and vector components of this invention, LacZ histochemical staining could not be used to titer the yield of recombinant AV.CMVLacZ since any contaminating Ad.AV.CMVLacZ hybrid would contribute to the final count. Therefore, a rapid Southern blot technique for quantitating yields of recombinant AAV was incorporated. The assay that was developed enabled not only quantitation and verification of AAV production, but also demonstrated the removal of contaminating hybrid virus from purified AAV stocks.

Another method for detecting contaminating hybrid virions involves modifying the hybrid vector by inserting a small second reporter minigene (i.e., reporter gene, promoter and other expression control sequences, where desired) into the E3 region of the parental adenovirus backbone. Because this reporter is not linked to the AAV domain, contaminating hybrid virus that is present during purification can be monitored by this hybrid-specific marker. Another possible reporter gene is the nucleic acid sequence for green fluorescent protein. With this hybrid vector containing two reporter sequences, histochemical staining for alkaline phosphatase (adenovirus reporter) or β-galactosidase (AAV reporter) activity can be used to monitor each viral domain.

The following examples illustrate the construction and testing of the hybrid vectors of the present invention and the use thereof in the productions of recombinant AAV. These examples are illustrative only, and do not limit the scope of the present invention.

EXAMPLE 1

Construction of a Hybrid Virus

A first hybrid adenovirus-AAV virus was engineered by homologous recombination between DNA extracted from an adenovirus and a complementing vector according to protocols previously described [see, e.g., K. F. Kozarsky et al, *J. Biol. Chem.*, 269:13695–13702 (1994) and references cited therein]. The following description refers to the diagram of FIG. 1.

Adenovirus DNA was extracted from CsCl purified d17001 virions, an Ad5 (serotype subgroup C) variant that carries a 3 kb deletion between mu 78.4 through 86 in the nonessential E3 region (provided by Dr. William Wold, Washington University, St. Louis, Miss.). Adenoviral DNA was prepared for co-transfection by digestion with ClaI (adenovirus genomic bp position 917) which removes the left arm of the genome encompassing adenovirus map units 0–2.5. See lower diagram of FIG. 1B.

The complementing hybrid vector, pAd.AV.CMVLacZ (see FIG. 1A and FIG. 2 [SEQ ID NO: 1]) was constructed as follows:

A parental cloning vector, pAd.BglII was designed. It contains two segments of wild-type Ad5 genome (i.e., map units 0–1 and 9–16.1) separated by a unique BglII cloning site for insertion of heterologous sequences. The missing Ad5 sequences between the two domains (adenovirus genome bp 361–3327) results in the deletion of E1a and the majority of E1bfollowing recombination with viral DNA.

A recombinant AAV genome (AV.CMVLacZ) was designed and inserted into the BglII site of pAd.BglII to generate the complementing plasmid. The linear arrangement of AV.CMVLacZ [SEQ ID NO: 1] (see top diagram of FIG. 1B) includes:

(a) the 5' AAV ITR (bp 1–173) obtained by PCR using pAV2 [C. A. Laughlin et al, *Gene*, 23: 65–73 (1983)] as template (nucleotide numbers 365–538 of FIG. 2 [SEQ ID NO: 1]];

(b) a CMV immediate early enhancer/promoter [Boshart et al, *Cell*, 41:521–530 (1985); nucleotide numbers 563–1157 of FIG. 2 [SEQ ID NO: 1]], (c) an SV40 splice donor-splice acceptor (nucleotide numbers 1178–1179 of FIG. 2 [SEQ ID NO: 1]), (d) *E. coli* beta-galactosidase cDNA (nucleotide numbers 1356–4827 of FIG. 2 [SEQ ID NO: 1]), (e) an SV40 polyadenylation signal (a 237 Bam HI-BclI restriction fragment containing the cleavage/poly-A signals from both the early and late transcription units; nucleotide numbers 4839–5037 of FIG. 2 [SEQ ID NO: 1]) and (f) 3'AAV ITR, obtained from pAV2 as a SnaBI-BglII fragment (nucleotide numbers 5053–5221 of FIG. 2 [SEQ ID NO: 1]).

The resulting complementing hybrid vector, pAd.AV.C-MVLacZ (see FIG. 1A and FIG. 2 [SEQ ID NO: 1]), contained a single copy of recombinant AV.CMVLacZ flanked by adenovirus coordinates 0–1 on one side and 9–16.1 on the other. Plasmid DNA was linearized using a unique NheI site immediately 5' to adenovirus map unit zero (0) (resulting in the top diagram of FIG. 1B).

Both the adenovirus substrate and the complementing vector DNAs were transfected to 293 cells [ATCC CRL1573] using a standard calcium phosphate transfection procedure [see, e.g., Sambrook et al, cited above]. The end result of homologous recombination involving sequences that map to adenovirus map units 9–16.1 is hybrid Ad.AV.C-MVLacZ (see FIG. 1C) in which the E1a and E1bcoding regions from the dl7001 adenovirus substrate are replaced with the AV.CMVLacZ from the hybrid vector.

Twenty-four hours later, the transfection cocktail was removed and the cells overlayed with 0.8% agarose containing 1× BME and 2% fetal bovine serum (FBS). Once viral plaques developed (typically 10–12 days post-transfection), plaques were initially screened for *E. coli* β-galactosidase (LacZ) activity by overlaying the infected monolayer with agarose supplemented with a histochemical stain for LacZ, according to the procedure described in J. Price et al, *Proc. Natl. Acad. Sci., USA*, 84:156–160 (1987).

Positive clones (identified by the deposit of insoluble blue dye) were isolated, subjected to three rounds of freeze (dry ice/ethanol)-thaw (37° C.) and an aliquot of the suspended plaque was used to infect a fresh monolayer of 293 cells seeded on duplicate 60mm plates.

Twenty-four hours later the cells from one set of plates were fixed and again stained for LacZ activity. Cells from the duplicate plate were harvested, suspended in 0.5 ml 10 mM Tris-Cl, pH8.0, and lysed by performing a series of three freeze (dry ice/ethanol)-thaw (37° C.) cycles. Cell debris was removed by centrifugation and an aliquot of the supernatant used to measure LacZ enzyme activity.

As indicated in FIG. 3, assays for β-galactosidase activity which measured the absorbance at 420 nm of the beta-galactosidase blue color in successful recombinants, revealed that eight of the ten isolated, putative positive clones (D1A through D1A) expressed high levels of enzyme. Histochemical staining produced similar results.

Large-scale production and purification of recombinant virus was performed as described in Kozarsky et al, cited above, and references cited therein.

EXAMPLE 2
Functional Analysis of Hybrid Vector

The ability to rescue the AV.CMVLacZ sequence [SEQ ID NO: 1] from the hybrid virus represented an important feature of the hybrid vector and virus systems of Example 1. To evaluate this feature, it was necessary to provide the necessary AAV gene products in trans that direct AAV excision and amplification (i.e. rep proteins). Furthermore, this experiment was conducted in 293 cells to transcomplement the E1 deletion in the Ad.AV.CMVLacZ clones, because the adenovirus E1 gene proteins have been shown to be important for initiating the lytic phase of the AAV lifecycle.

293 cells were seeded onto 6-well 35 mm plates at a density of $1 \times 10^6$ cells/well. Twenty-four hours later, seeding media (DMEM/10% FBS supplemented with antibiotics) was replaced with 1.0 ml DMEM/2% FBS and infected with Ad.AV.CMVLacZ hybrid clones at an MOI of 1.

Two hours later, each well was transfected with 1 μg plasmid pRep78/52 [SEQ ID NO: 2], a trans-acting plasmid that encodes the sequence encoding the AAV rep 78 kD and 52 kD proteins. The rep sequences in this construct are under the control of the AAV P5 promoter and utilize an SV40 polyadenylation signal.

As a positive control for AAV rescue, 293 cells seeded in a 6-well plate as above were co-transfected with a cis-acting AAV plasmid pAV.CMVLacZ and pRep78/52. pAV.CMV-LacZ contained AV.CMVLacZ, the identical sequence encoded by pAd.AV.CMVLacZ [SEQ ID NO: 1] described in Example 1 cloned into the BglII site of pSP72 (Promega).

To provide the necessary adenovirus helper function for AAV rescue, cells were infected with either wild-type Ad5 virus or a first generation E1-deleted virus Ad.CMhpAP at an MOI of 5, approximately 2 hours prior to adding the transfection cocktail. Ad.CMhpAP is identical to Ad.CMV-LacZ (Example 1) with the modification that the alkaline phosphatase sequence (which can be obtained from Genbank) is inserted in place of the LacZ gene.

Transfections were performed with Lipofectamine (Life Technologies) according to the instructions provided by the manufacturer. Thirty hours post-transfection, the cells were harvested and episomal DNA (Hirt extract) prepared as described by J. M. Wilson et al, *J. Biol. Chem.*, 267:(16) :11483–11489 (1992). Samples were resolved on a 1.2% agarose gel and electroblotted onto a nylon membrane. Blots were hybridized (Southern) with a $^{32}$p random primer-labeled restriction fragment isolated from the *E. coli* LacZ cDNA.

The full spectrum of duplex molecular species that appear during a lytic AAV infection (i.e., monomeric forms of the double stranded intermediates, RFm and RFd, respectively) were evident in transfected cells infected with wild type and E1 deleted Ad5. No replicative intermediates were detected when transfections were performed in the absence of helper virus.

Hirt extracts from the 293 cells infected with putative Ad.AV.CMVLacZ hybrid clones D1A and D1C revealed a single band corresponding to the viral DNA, when probed with a LacZ restriction fragment. In the presence of rep proteins 78 and 52, however, the same clones yielded a banding pattern that included not only the adenovirus DNA, but an RF monomer and dimer of AV.CMVLacZ. A single-stranded form of AV.CMVLacZ [SEQ ID NO: 1] was not evident. Two additional clones gave similar banding patterns, D1B and D1H. In all, each of the eight Ad.AV.C-MVLacZ hybrids that were found in FIG. 3 to express high levels of Lac Z activity were positive for rescue of the AAV domain.

With the exception of an extra band of approximately 3.5 kb, the rescue of the AV.CMVLacZ [SEQ ID NO: 1] from the hybrid viral DNA was nearly identical to results obtained from a standard cis and trans plasmid-based approach. In these later samples, adenovirus helper function was provided by pre-infecting cells with either wild-type Ad5 or an E1-deleted recombinant virus Ad.CBhpAP (also termed H5.CBALP). The Ad.CBhpAP virus has the same sequence as the Ad.CMhpAP virus described above, except that the CMV promoter sequence is replaced by the chicken cytoplasmic β-actin promoter [nucleotides +1 to +275 as described in T. A. Kost et al, *Nucl. Acids Res.*, 11(23):8287 (1983)]. The level of rescue in cells infected with WT Ad5 appeared to be greater relative to those infected with the recombinant Ad.CBhpAP virus, likely due to the additional E1 expression provided by the wild-type genome. The relevance of including an E1 deleted adenovirus here is to document that the level of adenovirus E1 proteins expressed in 293 cells is sufficient for AAV helper function.

EXAMPLE 3

Synthesis of Polylysine Conjugates

Another version of the viral particle of this invention is a polylysine conjugate with a rep plasmid completed directly to the hybrid virus capsid. This conjugate permits efficient delivery of the rep expression plasmid pRep78/52 [SEQ ID NO: 2] in tandem with the hybrid virus, thereby removing the need for a separate transfection step. See, FIG. 8 for a diagrammatic outline of this construction.

Purified stocks of a large-scale expansion of Ad.AV.CM-VLacZ clone D1A were modified by coupling poly-L-lysine to the virion capsid essentially as described by K. J. Fisher and J. M. Wilson, *Biochem. J.*, 299:49–58 (1994), resulting in an Ad.AV.CMVLacZ-(LyS)$_n$ conjugate.

The procedure involves three steps. First, hybrid virions are activated through primary amines on capsid proteins with the heterobifunctional water-soluble cross-linking agent, sulpho-SMCC [sulpho-(N-succinimidyl 4-(N-maleimidomethyl)-cyclohexane-1-carboxylate] (Pierce). The conjugation reaction, which contained 0.5 mg (375 nmol) of sulpho-SMCC and $6 \times 10^{12}$ A$_{260}$ hybrid vector particles in 3.0 ml of HBS, was incubated at 30° C. for 45 minutes with constant gentle shaking. This step involved formation of a peptide bond between the active N-hydroxysuccinimide (NHS) ester of sulpho-SMCC and a free amine (e.g. lysine) contributed by an adenovirus protein sequence (capsid protein) in the recombinant virus, yielding a maleimide-activated viral particle.

Unincorporated, unreacted cross-linker was removed by gel filtration on a 1 cm×15 cm Bio-Gel P-6DG (Bio-Rad Laboratories) column equilibrated with 50 mM Tris/HCl buffer, pH 7.0, and 150 mM NaCl. Peak A$_{260}$ fractions containing maleimide-activated hybrid virus were combined and placed on ice.

Second, poly-L-lysine having a molecular mass of 58 kDa at 10 mg/ml in 50 mM triethanolamine buffer (pH 8.0), 150 mM NaCl and 1 mM EDTA was thiolated with 2imminothiolane/HCl (Traut's Reagent; Pierce) to a molar ratio of 2 moles-SH/mole polylysine under N$_2$; the cyclic thioimidate reacts with the poly(L-lysine) primary amines resulting in a thiolated polycation. After a 45 minute incubation at room temperature the reaction was applied to a 1 cm×15 cm Bio-Gel P6DG column equilibrated with 50 mM Tris/HCl buffer (pH 7.0), 150 mM NaCl and 2 mM EDTA to remove unincorporated Traut's Reagent.

Quantification of free thiol groups was accomplished with Ellman's reagent [5,5'-dithio-bis-(2-nitrobenzoic acid)], revealing approximately 2 mol of -SH/mol of poly(L-lysine). The coupling reaction was initiated by adding $1 \times 10^{12}$ A$_{260}$ particles of maleimide-activated hybrid virus/ mg of thiolated poly(L-lysine) and incubating the mixture on ice at 4° C. for 15 hours under argon. 2-mercaptoethylamine was added at the completion of the reaction and incubation carried out at room temperature for 20 minutes to block unreacted maleimide sites.

Virus-polylysine conjugates, Ad.AV. CMVLacZ-(Lys)$_n$, were purified away from unconjugated poly(L-lysine) by ultracentrifugation through a CsCl step gradient with an initial composition of equal volumes of 1.45 g/ml (bottom step) and 1.2 g/ml (top step) CsCl in mM Tris/HCl buffer (pH 8.0). Centrifugation was at 90,000 g for 2 hours at 5° C. The final product was dialyzed against 20 mM Hepes buffer (pH 7.8) containing 150 mM NaCl (HBS).

Complexes of Ad.AV.CMVLacZ-(Lys)$_n$ with pRep78/52 plasmid DNA [SEQ ID NO: 2] were formed by adding varying quantities of Ad.AV.CMVLacZ-(Lys)$_n$ in 50 μl HBS to 0.5 g of pRep78/52 plasmid DNA [SEQ ID NO: 2] in 50 μl HBS. After 30 minutes incubation at room temperature, a complex was formed of the hybrid virus Ad.AV.CMVLacZ-(Lys)$_n$ associated in a single particle with the plasmid DNA containing the rep genes.

This complex, termed a trans-infection particle, was evaluated for DNA binding capacity by gel mobility shift assays performed as described in Fisher et al, cited above. This analysis revealed that the plasmid binding capacity of the purified conjugate (expressed as the number of A$_{260}$ particles Ad.AV.CMVLacZ-(Lys)$_n$ that can neutralize the charge contributed by 1 μg plasmid DNA) was 1 μg pRep78/52 plasmid DNA/$6.0 \times 10^{10}$ A$_{260}$ particles Ad.AV.CMVLacZ-(Lys)$_n$.

EXAMPLE 4

Trans-Infection Protocol to Demonstrate AAV Excision and Amplification

Trans-infection complexes were prepared by mixing Ad.AV.CMVLacZ-(Lys)$_n$ conjugate with pRep78/52 plasmid [SEQ ID NO: 2] and applied to 293 cells as follows. Ad.AV.CMVLacZ-(Lys)$_n$ ($6 \times 10^{10}$ A$_{260}$ particles) in 100 μl DMEM was added dropwise to a microfuge tube containing 1 μg plasmid DNA in 100 μl DMEM. The mixture was gently mixed and allowed to incubate at room temperature for 10–15 minutes. The trans-infection cocktail was added to 293 cells seeded in a 35 mm 6-well as detailed above. Thirty hours later, cells were harvested and Hirt extracts prepared.

Samples were resolved on a 1.2% agarose gel and lectroblotted onto a nylon membrane. Blots were hybridized (Southern) with a P-32 random primer-labeled restriction fragment isolated from the E. coli LaCZ CDNA.

The Hirt extracts from 293 cells revealed a landing pattern that suggested the AV.CMVLacZ minigene sequence [SEQ ID NO: 1] was efficiently rescued from the hybrid conjugate. Both an RF monomer and dimer of the recombinant AV.C-MVLacZ sequence were evident. As was observed previously, the rescue event was dependent on rep proteins since 293 cells that were trans-infected with a hybrid conjugate complexed with an irrelevant reporter plasmid expressing alkaline phosphatase (i.e. pCMVhpAP) revealed only Ad.AV.CMVLacZ DNA. This negative control for rescue was secondarily useful for demonstrating the high efficiency of gene transfer to 293 cells that was achieved with the conjugate vehicle.

A duplicate set of 293 cells that received hybrid conjugate which was further complexed with alkaline phosphatase expression plasmid were fixed 24 hours after addition of the trans-infection cocktail and histochemically stained for LacZ as described in Price et al, cited above, or for alkaline phosphatase activity as described in J. H. Schreiber et al, BioTechnigues, 14:818–823 (1993). Here LacZ was a marker for the Ad.AV.CMVLacZ hybrid, while alkaline phosphatase served as a reporter for the carrier plasmid. Greater than 90% of the monolayer was transduced with both β-galactosidase and alkaline phosphatase transgenes, showing the high efficiency of the conjugate delivery vehicle (differential staining revealed a blue color for the hybrids containing the LacZ marker and a purple color for the plasmids bearing the AP marker).

Because of the important role E1 proteins have for progression of the AAV lifecycle, it was critical to test the efficiency of the hybrid delivery system in a setting where E1 proteins are not expressed. A trans-infection experiment using the hybrid conjugate complexed with pRep78/52 [SEQ ID NO: 2] was therefore conducted in HeLa cells [ATCC CC2] to remove the involvement of E1 proteins. The findings suggested rescue of AV.CMVLacZ occurred evidenced by the accumulation of RF monomers and dimers. Rescue from HeLa cells (which unlike the 293 cells do not contain any adenovirus E1 proteins) revealed lower levels of rescue of the transgene. The expression of rep from the AAV P5 promoter is upregulated by adenovirus E1 and signals the beginning of the AAV lytic cycle. In the absence of E1, rep expression from the P5 promoter is virtually silent which is important for maintenance of the proviral latent stages of the AAV lifecycle. It is anticipated that a promoter not dependent on E1 expression will upon substitution for P5, overcome this problem.

EXAMPLE 5
Integration of the Transgene

A preliminary study has been performed to determine whether the AAV sequence rescued from the hybrid virus can achieve provirus status in a target cell (FIG. 7). Briefly, HeLa cells [ATCC CCL 2) were infected with the hybrid conjugate completed with pRep78/52 [SEQ ID NO: 2] and passaged until stable colonies of LacZ expressing cells were evident. A duplicate plate of cells was infected with the same conjugate, but instead of being complexed with the pRep78/52 plasmid [SEQ ID NO: 2], carried an irrelevant plasmid. These findings indicated that cells that received the Rep containing hybrid particle produced a greater number of stable LacZ positive colonies than cells that were infected with the control virus. This could be interpreted as a reflection of multiple rescue and integration events in cells that expressed Rep proteins. However, it is possible that an pepisomal form of AAV that can persist for extended periods of time was present.

To establish the occurrence of integration into the chromosome of the minigene AV.CMVLacZ from the hybrid conjugate, the following experiment is performed. The Ad.AV.CMVLacZ-(Lys)$_n$ conjugate carrying pRep78/52 plasmid [SEQ ID NO: 2] is used to infect HeLa cells [ATCC CRL2] (primary fibroblasts may also be used). The infected cells are passaged for several generations. The cells are grown to confluency, split and allowed to grow to confluency again, split again and this cycle repeated as desired. This permits sufficient time for uptake, expression, replication and integration to occur. See FIG. 7.

To verify that the recombinant AAV sequence that was rescued from the hybrid genome (step III of FIG. 7) has integrated into a chromosome of the host cell (step IV of FIG. 7), cells are separated by a Fluorescence Activated Cell Sorter (FACS). By this technique, those cells containing a stable integrated copy of the recombinant AV.CMVLacZ minigene are separated based on the presence of the β-galactosidase reporter. These cells are tagged with fluorescein-labeled antibodies that recognize the β-Gal protein, and are then separated from non-transduced cells (i.e. those that did not receive a copy of the AAV minigene) by FACS.

DNA is isolated from this purified population of cells and used to construct a genomic library which is screened for individual clones and the sequence verified. If integration occurs, it is documented directly by sequence analysis.

EXAMPLE 6
Gene Transfer Vehicle for Cystic Fibrosis

An adenovirus-AAV-CFTR virus constructed by modifying the hybrid Ad.AV.CMVlacZ virus described in Example 1 to contain the cystic fibrosis transmembrane regulator (CFTR) gene (J. R. Riordan et al, Science. 245:1066–1073 (1989)] in place of the lacZ gene, using known techniques. One suitable method involves producing a new vector using the techniques described in Example 1. In this new vector the LacZ minigene is replaced with the CFTR minigene. For performance of this method vectors bearing the CFTR gene have been previously described and can be readily constructed. This new or reconstructed vector is used to generate a new virus through homologous recombination as described above. The resulting hybrid virus is termed hybrid Ad.AV.CMVCFTR. It has the sequence of FIG. 2 [SEQ ID NO: 1], except that the LacZ gene is replaced with CFTR. Alternatively, the LacZ gene can be removed from the Ad.AV.CMVLacZ vector of Example 1 and replaced with the CFTR gene using known techniques.

This virus (or an analogous hybrid virus with a different promoter, regulatory regions, etc.) is useful in gene therapy alone, or preferably, in the form of a conjugate prepared as described in Example 4.

Treatment of cystic fibrosis, utilizing the viruses provided above, is particularly suited for in vivo, lung-directed, gene therapy. Airway epithelial cells are the most desirable targets for gene transfer because the pulmonary complications of CF are usually its most morbid and life-limiting. Thus, the hybrid vector of the invention, containing the CFTR gene, is delivered directly into the airway, e.g. by formulating the hybrid virus above, into a preparation which can be inhaled. For example, the hybrid virus or conjugate of the invention containing the CFTR gene, is suspended in 0.25 molar sodium chloride. The virus or conjugate is taken up by respiratory airway cells and the gene is expressed.

Alternatively, the hybrid viruses or conjugates of the invention may be delivered by other suitable means, including site-directed injection of the virus bearing the CFTR gene. In the case of CFTR gene delivery, preferred solutions for bronchial instillation are sterile saline solutions containing in the range of from about $1\times10^7$ to $1\times10^{10}$ pfu/ml, more particularly, in the range of from about $1\times10^8$ to $1\times10^9$ pfu/ml of the recombinant hybrid virus of the present invention.

Other suitable methods for the treatment of cystic fibrosis by use of gene therapy recombinant viruses of this invention may be obtained from the art discussions of other types of gene therapy vehicles for CF. See, for example, U.S. Pat. No. 5,240,846, incorporated by reference herein.

EXAMPLE 7
Gene Transfer Vehicle for Familial Hypercholesterolemia

Familial hypercholesterolemia (FH) is an autosomal dominant disorder caused by abnormalities (deficiencies) in the function or expression of LDL receptors [M. S. Brown and J. L. Goldstein, *Science*, 232(4746):34–37 (1986); J. L. Goldstein and M. S. Brown, "Familial hypercholesterolemia" in *Metabolic Basis of Inherited Disease.*, ed. C. R. Scriver et al, McGraw Hill, New York, pp1215–1250 (1989).] Patients who inherit one abnormal allele have moderate elevations in plasma LDL and suffer premature life-threatening coronary artery disease (CAD). Homozygous patients have severe hypercholesterolemia and life-threatening CAD in childhood.

A hybrid adenovirus-AAV-LDL virus of the invention is constructed by replacing the lacZ gene in the hybrid Ad.AV.CNVlacZ virus of Example 1 with an LDL receptor gene [T. Yamamoto et al, *Cell*, 39:27–38 (1984)] using known techniques and as described analogously for CF in the preceding example. Vectors bearing the LDL receptor gene can be readily constructed according to this invention. The resulting hybrid vector is termed pAd.AV.CMVLDL.

This plasmid or its recombinant virus is useful in gene therapy of FH alone, or preferably, in the form of a viral conjugate prepared as described in Example 4 to substitute a normal LDL gene for the abnormal allele responsible for the gene.

A. Ex Vivo Gene Therapy

Ex vivo gene therapy can be performed by harvesting and establishing a primary culture of hepatocytes from a patient. Known techniques may be used to isolate and transduce the hepatocytes with the above vector(s) bearing the LDL receptor gene(s). For example, techniques of collagenase perfusion developed for rabbit liver can be adapted for human tissue and used in transduction. Following transduction, the hepatocytes are removed from the tissue culture plates and reinfused into the patient using known techniques, e.g. via a catheter placed into the inferior mesenteric vein.

B. In Vivo Gene Therapy

Desirably, the in vivo approach to gene therapy, e.g. liver-directed, involves the use of the hybrid viruses and viral conjugates described above. A preferred treatment involves infusing a trans-infection particle of the invention containing LDL into the peripheral circulation of the patient. The patient is then evaluated for change in serum lipids and liver tissues.

The hybrid virus or viral conjugate can be used to infect hepatocytes in vivo by direct injection into a peripheral or portal vein ($10^7$–$10^8$ pfu/kg) or retrograde into the biliary tract (same dose). This effects gene transfer into the majority of hepatocytes.

Treatments are repeated as necessary, e.g. weekly. Administration of a dose of virus equivalent to an MOI of approximately 20 (i.e. 20 pfu/hepatocyte) is anticipated to lead to high level gene expression in the majority of hepatocytes.

EXAMPLE 8
Efficient Production of Recombinant AAV using A Hybrid VirusiConjugate The following experiment demonstrated that the AAV genome that was rescued from the Ad.AV.CMVLacZ hybrid virus could be packaged into an AAV capsid, provided the cap open reading frame was supplied in trans. Thus the viruses of this invention are useful in a production method for recombinant AAV which overcomes the prior art complications that surround the high titer production of recombinant AAV.

A. Trans-Infection Protocol for the Production of rAAV

A trans-infection complex was formed composed of the Ad.AV.CMVLacZ-(Lys)$_n$ conjugate described above and a transcomplementing plasmid pAdAAV, which is described in detail in R. J. Samulski et al, *J. Virol.*, 63(9):3822–3828 (1989)]. Briefly, plasmid pAdAAV encodes the entire rep and cap open reading frames in the absence of AAV ITRS, and has been shown to provide the necessary AAV helper functions for replication and packaging of recombinant AAV sequences.

Ad.AV.CMVLacZ-(Lys)$_n$ conjugate ($4\times10^{13}$ A$_{260}$ particles) in 75 ml DMEM was added dropwise with constant gentle swirling in 25 ml DMEM containing 750 µg pAdAAV helper plasmid and incubated at room temperature for 10–15 minutes. The complex was diluted with 450 ml DMEM supplemented with 2% FBS and 20 ml aliquots were added to monolayers of 293 cells seeded on 150 mm plates.

Forty hours post transt-infection, cells were harvested, suspended in 12 ml 10 mM Tris-Cl (pH 8.0), and stored at −80° C.

Because the anticipated outcome was the production of hybrid virus Ad.AV.CMVLacZ and a recombinant AAV virion (AV.CMVLacZ), both of which carry a functional LacZ minigene, it was not possible to use detection of LacZ activity as an indicator of AV.CMVLacZ production. A novel molecular approach was developed that could be performed in one day and permitted identification of the packaged viral DNAS.

B. Purification of rAAV

Briefly, frozen cell suspensions were subjected to three rounds of freeze-thaw cycles to release recombinant AV.C-MVLacZ and hybrid Ad.AV.CMVLacZ. On completion of the final thaw, bovine pancreatic DNAse (2000 units) and ribonuclease (0.2 mg/ml final concentration) was added and the extract incubated at 37° C. for 30 minutes. Cell debris was removed by centrifugation (5000×g for 10 minutes) and the clarified supernatant (15 ml) applied to a 22.5 ml step gradient composed of equal volumes of CsCl at 1.2 g/ml, 1.36 g/ml, and 1.45 g/ml 10mM Tris-Cl, pH8.0. Viral particles were banded at 25,000 rpm in a Beckman SW-28 rotor for 8 hours at 4° C. One ml fractions were collected from the bottom of the tube.

The fractions retrieved from the CsCl gradient of partially purified virus are then digested to release viral DNA from virion capsids as follows. A 5.1 µl sample of each fraction was transferred to a microfuge tube containing 20 µl capsid digestion buffer (50 mM Tris-Cl, pH8.0, 1.0 mM EDTA, pH8,0, 0.5% SDS, and 1.0 mg/ml Proteinase K). The reaction was incubated at 50° C. for 1 hour, allowed to cool to room temperature, diluted with 10 µl milli-Q water, and agarose gel loading dye added.

These fractions are then analyzed by Southern blotting. Samples were resolved on a 1.2% agarose gel, electroblotted onto a nylon membrane. A $^{32}$p labeled LacZ restriction fragment which was common to both vectors was used as a hybridization probe to locate the migration of viral DNA through the agarose gel. Viral bands were quantitated on a Molecular Dynamics Phosphoimager.

A sample of the extract before CsCl banding was also tested and revealed both hybrid Ad.AV.CMVLacZ DNA and double-stranded RF forms (monomers and dimers) of the rescued AV.CMVLacZ sequence [SEQ ID NO: 1]. A single-stranded monomer of AV.CMVLacZ appeared to be present in the crude extract; however, it was not until the virions were concentrated by buoyant density ultracentrifugation that the single-stranded genome became clearly evident. The single-stranded recombinant genome of the virus was distributed over a range of CsCl densities and revealed a biphasic banding pattern. The two peaks of single-stranded rAAV genome occurred at densities of 1.41 and 1.45 g/ml CsCl, consistent with the reported buoyant densities of wild-type AAV in CsCl [L. M. de la Maza et al, *J. Virol.*, 33:1129–1137 (1980)]. Analysis of the fractions corresponding to the two vector forms revealed the rAAV-1.41 species was several orders of magnitude more active for lacZ transduction than the denser rAAV-1.45 g/ml variant. To avoid confusion with contaminating Ad.AAV, samples were heat inactivated (60° C. for 30 min) before being added to indicator HeLa cells.

The peak fractions of rAAV-1.41 were combined and purified by equilibrium sedimentation in CsCl to eliminate residual adenovirus particles and concentrate rAAV virions. On the final round of ultracentrifugation, a faint but clearly visible opalescent band was observed in the middle of the gradient tube. Fractions that surrounded the band were evaluated for density, absorbance at 260 nm, and lacZ transducing particles. As the band eluted from the gradient tube, a well defined peak of 260 nm absorbing material was recorded, with a maximal absorbance occurring at a density of 1.40 g/ml CsCl. Analysis for lacz transducing particles on HeLa cells revealed a peak of activity that mirrored the absorbance profile. These results indicate rAAV was produced from the hybrid Ad.AAV virus. Furthermore, the titers achieved using the hybrid virus were 5–10 fold elevated compared to more conventional recombinant AAV production schemes (i.e., transfections with cis- and trans-acting plasmids). This represents a significant improvement in rAAV production and indicates that the hybrid is useful for large-scale rAAV production.

All references recited above are incorporated herein by reference. Numerous modifications and variations of the present invention are included in the above-identified specification and are expected to be obvious to one of skill in the art. Such modifications and alterations to the compositions and processes of the present invention, such as those modifications permitting optimal use of the hybrid viruses as gene therapy vehicles or production vehicles for recombinant AAV production, are believed to be encompassed in the scope of the claims appended hereto.

---

What is claimed is:

1. A recombinant hybrid virus comprising:
   (a) adenovirus sequences comprising the adenovirus 5' and 3' cis-elements necessary for replication and virion encapsidation;
   (b) adeno-associated virus (AAV) sequences comprising the 5' and 3' inverted terminal repeats (ITRs) of an AAV, said AAV sequences flanked by the adenovirus sequences of (a); and
   (c) a selected transgene operatively linked to sequences which regulate its expression in a target cell, said gene and regulatory sequences flanked by the AAV sequences of (b);
      wherein the adenovirus sequences comprise a functional deletion in the adenovirus E1 gene, the adenovirus E3 gene, and the adenovirus E4 gene, and
      wherein the hybrid virus is provided with sufficient adenovirus sequences to permit packaging into a capsid and infection of a target cell.

2. The recombinant hybrid virus according to claim 1, wherein said virus comprises adenovirus sequences having a functional deletion in one or more of the adenovirus genes selected from the group consisting of the E2 gene, intermediate gene IX, intermediate gene IXa, and any of the late genes L1 through L5.

3. The recombinant hybrid virus according to claim 1, wherein the AAV sequences (b) and transgene (c) form a minigene of about 8 kb to about 30 kb in size.

4. The recombinant hybrid virus according to claim 1, wherein the transgene is a therapeutic gene.

5. The recombinant hybrid virus according to claim 1, wherein the hybrid virus further comprises an AAV rep gene in the site of a deletion of adenoviral sequences.

6. A composition comprising a recombinant hybrid virus according to claim 1 and a pharmaceutically acceptable carrier.

7. The recombinant hybrid virus according to claim 2, wherein said functional deletions in the E1 gene and E2 gene are selected from one or more of E1a, E1b, E2a, and E2b.

8. The recombinant hybrid virus according to claim 2, wherein the hybrid virus contains functional deletions in all adenoviral genes.

9. The recombinant hybrid virus according to claim 3, wherein said transgene regulatory sequences comprise a promoter and enhancer.

10. The recombinant hybrid virus according to claim 9, wherein the transgene is a reporter gene.

11. The recombinant hybrid virus according to claim 10, wherein the reporter gene is selected from the group consisting of the genes encoding β-galactosidase, alkaline phosphatase and green fluorescent protein.

12. The recombinant hybrid virus according to claim 4, wherein the therapeutic gene is selected from the group consisting of a CFTR gene and an LDL receptor gene.

13. A recombinant hybrid virus comprising:
   (a) adenovirus sequences comprising the adenovirus 5' and 3' cis-elements necessary for replication and virion encapsidation;
   (b) adeno-associated virus (AAV) sequences comprising the 5' and 3' inverted terminal repeats (ITRs) of an AAV, said AAV sequences flanked by the adenovirus sequences of (a); and
   (c) a selected transgene operatively linked to sequences which regulate its expression in a target cell, said gene and regulatory sequences flanked by the AAV sequences of (b);
      wherein the adenovirus sequences comprise a functional deletion in the adenovirus E1 gene, the adenovirus E2 gene, the adenovirus E3 gene, and the adenovirus E4 gene, intermediate gene IX, intermediate gene IXa, and late genes L1 through L5; and
      wherein the hybrid virus is provided with sufficient adenovirus sequences to permit packaging into a capsid and infection of a target cell.

14. The recombinant hybrid virus according to claim 13, wherein said functional deletions in the E1 gene and E2 gene are selected from one or more of E1a, E1b, E2a, and E2b.

15. The recombinant hybrid virus according to claim 13, wherein the hybrid virus contains functional deletions in all adenoviral genes.

16. The recombinant hybrid virus according to claim 13, wherein the AAV sequences of (b) and the transgene (c) form a minigene of about 8 kb to about 30 kb in size.

17. The recombinant hybrid virus according to claim 13, wherein the transgene is a reporter gene.

18. The recombinant hybrid virus according to claim 13, wherein the transgene is a therapeutic gene.

19. The recombinant hybrid virus according to claim 13, wherein the hybrid virus further comprises an AAV rep gene in the site of a deletion of adenoviral sequences.

20. A composition for use in delivering a selected transgene into the chromosome of a target cell, said composition comprising a recombinant hybrid virus according to claim 13 and a pharmaceutically acceptable carrier.

21. A mammalian host cell comprising the virus of claim 1 or claim 13.

22. The recombinant hybrid virus according to claim 16, wherein said transgene regulatory sequences comprise a promoter and enhancer.

23. The recombinant hybrid virus according to claim 17, wherein the reporter gene is selected from the group consisting of the genes encoding β-galactosidase, alkaline phosphatase and green fluorescent protein.

24. The recombinant hybrid virus according to claim 18, wherein the therapeutic gene is selected from the group consisting of a CFTR gene and an LDL receptor gene.

25. The composition according to claim 6, wherein said hybrid virus comprises adenovirus sequences having a functional deletion in one or more of the adenovirus genes selected from the group consisting of E1a, E1b, E2a, E2b, intermediate gene IX, intermediate gene IXa, and any of the late genes L1 through L5.

26. The composition according to claim 6, wherein said composition comprises about 20 to about 50 ml saline.

27. The composition according to claim 6, wherein said composition comprises about $1 \times 10^7$ to about $1 \times 10^{10}$ pfu/ml of hybrid virus.

28. A recombinant hybrid vector comprising:
   (a) adenovirus sequences comprising the adenovirus 5' and 3' cis-elements necessary for replication and virion encapsidation;
   (b) adeno-associated virus (AAV) sequences comprising the 5' and 3' inverted terminal repeats (ITRs) of an AAV, said AAV sequences flanked by the adenovirus sequences of (a); and
   (c) a selected transgene operatively linked to sequences which regulate its expression in a target cell, said gene and regulatory sequences flanked by the AAV sequences of (b); and
      wherein the adenovirus sequences comprise a functional deletion in the adenovirus E1 gene, the adenovirus E3 gene, and the adenovirus E4 gene.

29. The recombinant hybrid vector according to claim 28, wherein said vector is functionally deleted of all adenovirus genes.

30. A method for producing a recombinant adeno-associated virus in a cell comprising the step of culturing a cell containing
   (a) a recombinant, replication-defective, hybrid virus comprising:
      (i) adenovirus sequences comprising the adenovirus 5' and 3' cis-elements necessary for replication and virion encapsidation,
      (ii) adeno-associated virus (AAV) sequences comprising the 5' and 3' inverted terminal repeat (ITRs) of an AAV, said AAV sequences flanked by the adenovirus sequences of (i); and
      (iii) a selected transgene operatively linked to sequences which regulate its expression in a target cell, said gene and regulatory sequences flanked by the AAV sequences of (ii),
         wherein the hybrid virus is provided with sufficient adenovirus sequences to permit packaging into a capsid and infection of a target cell;
   (b) an optional helper virus;
   (c) a rep gene under the control of sequences which regulate expression of said rep; and
   (d) a cap gene under the control of sequences which regulate expression of said cap.

31. The method according to claim 30, wherein the rep gene is provided by a plasmid.

32. The method according to claim 30, wherein the plasmid is pRep78/52 [SEQ ID NO:2].

33. The method according to claim 30, wherein the cap gene is provided by a plasmid.

34. The method according to claim 30, wherein the adenovirus sequences in the hybrid virus comprises a deletion in one or more of the adenovirus genes selected from the group consisting of the E1 a gene, the E1b gene, the E2a gene, the E3 gene, the E4 gene, intermediate gene IX and intermediate gene IXa, and any of the late genes L1 through L5.

35. The method according to claim 32 wherein pRep78/52 is enveloped in a liposome.

36. A method for producing a recombinant hybrid adenovirus comprising the step of culturing a host cell containing (a) a hybrid vector comprising:
  (i) adenovirus sequences comprising the adenovirus 5' and 3' cis-elements necessary for replication and virion encapsidation; and
  (ii) adeno-associated virus (AAV) sequences comprising the 5' and 3' inverted terminal repeat (ITRs) of an AAV, said AAV sequences flanked by the adenovirus sequences of (ii); and
  (iii) a selected transgene operatively linked to sequences which regulate its expression in a target cell, said gene and regulatory sequences flanked by the AAV sequences of (ii); and
(b) an optional helper adenovirus, wherein the host cell and/or the helper virus provide the adenovirus sequences necessary to package the hybrid vector and generate a recombinant hybrid adenovirus.

37. The method according to claim 36, further comprising the step of isolating from said culture the recombinant hybrid adenovirus.

38. The method according to claim 36, wherein the hybrid adenovirus contains functional deletions in one or more of the adenovirus genes selected from the group consisting of E1a, E1b, the E2 gene, the E3 gene, the E4 gene, intermediate gene IX, intermediate gene IVa, and any of late genes L1 through L5.

39. The method according to claim 38, wherein the hybrid adenovirus contains functional deletions in all adenovirus and adeno-associated virus genes.

* * * * *

UNITED STATES PATENT AND TRADEMARK OFFICE
CERTIFICATE OF CORRECTION

PATENT NO.    : 6,251,677 B1
DATED         : June 26, 2001
INVENTOR(S)   : James M. Wilson It is certified that error appears in the above-identified patent and that said Letters Patent is hereby corrected as shown below:

Title page,
Item [63], replace in its entirety with the following -- This is a continuation of US Patent Application No. 08/836,087, filed August 25, 1997, now US Patent 5,871,982, which was filed pursuant to 35 USC 371 as the national phase of PCT/US95/14018, filed October 25, 1994, which claims the priority of US Patent Application No. 08/331,384, filed October 28, 1994, now US Patent 5,856,152. --.

Column 5,
Line 8, replace "Ads," with -- Ad5, --.

Column 6,
Line 58, replace "E1 genes" with -- E1bgenes --.

Column 7,
Line 38, replace "E1a/E1genes" with -- E1a/E1bgenes --.

Column 9,
Line 46, replace "E1a/E1genes" with -- E1a/E1bgenes --.

Column 11,
Lines 61 and 62, replace "AAV P pro-moter," with -- AAV P5 promoter --.

Column 14,
Line 5, replace "09" with -- $10^9$ --.

Column 17,
Line 43, replace "completed" with -- complexed --.

Column 18,
Line 2, replace "l cm x$^{15}$ cm" with -- 1 cm x 15 cm --.
Line 31, replace "mM" with -- l0mM --.
Line 38, replace "0.5g" with -- 0.5µg --.

UNITED STATES PATENT AND TRADEMARK OFFICE
CERTIFICATE OF CORRECTION

PATENT NO. : 6,251,677 B1
DATED : June 26, 2001
INVENTOR(S) : James M. Wilson

It is certified that error appears in the above-identified patent and that said Letters Patent is hereby corrected as shown below:

Column 19,
Line 3, replace "landing" with -- banding --.
Line 36, replace "[ATCC CC2]" with -- [ATCC CCL2] --.
Line 66, replace "pepisomal" with -- episomal --.

Column 22,
Line 56, replace "5.1µl" with -- 5.0µl --.

Signed and Sealed this

Eleventh Day of February, 2003

JAMES E. ROGAN
*Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 10398 base pairs
      (B) TYPE: nucleic acid
      (C) STRANDEDNESS: double
      (D) TOPOLOGY: unknown (ii) MOLECULE TYPE: cDNA (xi) SEQUENCE DESCRIPTION: SEQ ID NO:1:

```
GAATTCGCTA GCATCATCAA TAATATACCT TATTTTGGAT TGAAGCCAAT              50

ATGATAATGA GGGGGTGGAG TTTGTGACGT GGCGCGGGGC GTGGGAACGG             100

GGCGGGTGAC GTAGTAGTGT GGCGGAAGTG TGATGTTGCA AGTGTGGCGG             150

AACACATGTA AGCGACGGAT GTGGCAAAAG TGACGTTTTT GGTGTGCGCC             200

GGTGTACACA GGAAGTGACA ATTTTCGCGC GGTTTTAGGC GGATGTTGTA             250

GTAAATTTGG GCGTAACCGA GTAAGATTTG GCCATTTTCG CGGGAAAACT             300

GAATAAGAGG AAGTGAAATC TGAATAATTT TGTGTTACTC ATAGCGCGTA             350

ATATTTGTCT AGGGAGATCT GCTGCGCGCT CGCTCGCTCA CTGAGGCCGC             400

CCGGGCAAAG CCCGGGCGTC GGGCGACCTT TGGTCGCCCG GCCTCAGTGA             450

GCGAGCGAGC GCGCAGAGAG GGAGTGGCCA ACTCCATCAC TAGGGGTTCC             500

TTGTAGTTAA TGATTAACCC GCCATGCTAC TTATCTACAA TTCGAGCTTG             550

CATGCCTGCA GGTCGTTACA TAACTTACGG TAAATGGCCC GCCTGGCTGA             600
```

-continued

| | |
|---|---|
| CCGCCCAACG ACCCCCGCCC ATTGACGTCA ATAATGACGT ATGTTCCCAT | 650 |
| AGTAACGCCA ATAGGGACTT TCCATTGACG TCAATGGGTG GAGTATTTAC | 700 |
| GGTAAACTGC CCACTTGGCA GTACATCAAG TGTATCATAT GCCAAGTACG | 750 |
| CCCCCTATTG ACGTCAATGA CGGTAAATGG CCCGCCTGGC ATTATGCCCA | 800 |
| GTACATGACC TTATGGGACT TTCCTACTTG GCAGTACATC TACGTATTAG | 850 |
| TCATCGCTAT TACCATGGTG ATGCGGTTTT GGCAGTACAT CAATGGGCGT | 900 |
| GGATAGCGGT TTGACTCACG GGGATTTCCA AGTCTCCACC CCATTGACGT | 950 |
| CAATGGGAGT TTGTTTTGGC ACCAAAATCA ACGGGACTTT CCAAAATGTC | 1000 |
| GTAACAACTC CGCCCCATTG ACGCAAATGG GCGGTAGGCG TGTACGGTGG | 1050 |
| GAGGTCTATA TAAGCAGAGC TCGTTTAGTG AACCGTCAGA TCGCCTGGAG | 1100 |
| ACGCCATCCA CGCTGTTTTG ACCTCCATAG AAGACACCGG GACCGATCCA | 1150 |
| GCCTCCGGAC TCTAGAGGAT CCGGTACTCG AGGAACTGAA AAACCAGAAA | 1200 |
| GTTAACTGGT AAGTTTAGTC TTTTTGTCTT TTATTTCAGG TCCCGGATCC | 1250 |
| GGTGGTGGTG CAAATCAAAG AACTGCTCCT CAGTGGATGT TGCCTTTACT | 1300 |
| TCTAGGCCTG TACGGAAGTG TTACTTCTGC TCTAAAAGCT GCGGAATTGT | 1350 |
| ACCCGCGGCC GCAATTCCCG GGATCGAAA GAGCCTGCTA AAGCAAAAAA | 1400 |
| GAAGTCACCA TGTCGTTTAC TTTGACCAAC AAGAACGTGA TTTTCGTTGC | 1450 |
| CGGTCTGGGA GGCATTGGTC TGGACACCAG CAAGGAGCTG CTCAAGCGCG | 1500 |
| ATCCCGTCGT TTTACAACGT CGTGACTGGG AAAACCCTGG CGTTACCCAA | 1550 |
| CTTAATCGCC TTGCAGCACA TCCCCCTTTC GCCAGCTGG GTAATAGCGA | 1600 |
| AGAGGCCCGC ACCGATCGCC CTTCCCAACA GTTGCGCAGC CTGAATGGCG | 1650 |
| AATGGCGCTT TGCCTGGTTT CCGGCACCAG AAGCGGTGCC GGAAAGCTGG | 1700 |
| CTGGAGTGCG ATCTTCCTGA GGCCGATACT GTCGTCGTCC CCTCAAACTG | 1750 |
| GCAGATGCAC GGTTACGATG CGCCCATCTA CACCAACGTA ACCTATCCCA | 1800 |
| TTACGGTCAA TCCGCCGTTT GTTCCCACGG AGAATCCGAC GGGTTGTTAC | 1850 |
| TCGCTCACAT TTAATGTTGA TGAAAGCTGG CTACAGGAAG GCCAGACGCG | 1900 |
| AATTATTTTT GATGGCGTTA ACTCGGCGTT TCATCTGTGG TGCAACGGGC | 1950 |
| GCTGGGTCGG TTACGGCCAG GACAGTCGTT TGCCGTCTGA ATTTGACCTG | 2000 |
| AGCGCATTTT TACGCGCCGG AGAAAACCGC CTCGCGGTGA TGGTGCTGCG | 2050 |
| TTGGAGTGAC GGCAGTTATC TGGAAGATCA GGATATGTGG CGGATGAGCG | 2100 |
| GCATTTTCCG TGACGTCTCG TTGCTGCATA AACCGACTAC ACAAATCAGC | 2150 |
| GATTTCCATG TTGCCACTCG CTTTAATGAT GATTTCAGCC GCGCTGTACT | 2200 |
| GGAGGCTGAA GTTCAGATGT GCGGCGAGTT GCGTGACTAC CTACGGGTAA | 2250 |
| CAGTTTCTTT ATGGCAGGGT GAAACGCAGG TCGCCAGCGG CACCGCGCCT | 2300 |
| TTCGGCGGTG AAATTATCGA TGAGCGTGGT GGTTATGCCG ATCGCGTCAC | 2350 |
| ACTACGTCTG AACGTCGAAA ACCCGAAACT GTGGAGCGCC GAAATCCCGA | 2400 |
| ATCTCTATCG TGCGGTGGTT GAACTGCACA CCGCCGACGG CACGCTGATT | 2450 |
| GAAGCAGAAG CCTGCGATGT CGGTTTCCGC GAGGTGCGGA TTGAAAATGG | 2500 |
| TCTGCTGCTG CTGAACGGCA AGCCGTTGCT GATTCGAGGC GTTAACCGTC | 2550 |
| ACGAGCATCA TCCTCTGCAT GGTCAGGTCA TGGATGAGCA GACGATGGTG | 2600 |

-continued

```
CAGGATATCC TGCTGATGAA GCAGAACAAC TTTAACGCCG TGCGCTGTTC        2650

GCATTATCCG AACCATCCGC TGTGGTACAC GCTGTGCGAC CGCTACGGCC        2700

TGTATGTGGT GGATGAAGCC AATATTGAAA CCCACGGCAT GGTGCCAATG        2750

AATCGTCTGA CCGATGATCC GCGCTGGCTA CCGGCGATGA GCGAACGCGT        2800

AACGCGAATG GTGCAGCGCG ATCGTAATCA CCCGAGTGTG ATCATCTGGT        2850

CGCTGGGGAA TGAATCAGGC CACGGCGCTA ATCACGACGC GCTGTATCGC        2900

TGGATCAAAT CTGTCGATCC TTCCCGCCCG GTGCAGTATG AAGGCGGCGG        2950

AGCCGACACC ACGGCCACCG ATATTATTTG CCCGATGTAC GCGCGCGTGG        3000

ATGAAGACCA GCCCTTCCCG GCTGTGCCGA ATGGTCCAT CAAAAAATGG         3050

CTTTCGCTAC CTGGAGAGAC GCGCCCGCTG ATCCTTTGCG AATACGCCCA        3100

CGCGATGGGT AACAGTCTTG GCGGTTTCGC TAAATACTGG CAGGCGTTTC        3150

GTCAGTATCC CCGTTTACAG GGCGGCTTCG TCTGGGACTG GGTGGATCAG        3200

TCGCTGATTA AATATGATGA AAACGGCAAC CCGTGGTCGG CTTACGGCGG        3250

TGATTTTGGC GATACGCCGA ACGATCGCCA GTTCTGTATG AACGGTCTGG        3300

TCTTTGCCGA CCGCACGCCG CATCCAGCGC TGACGGAAGC AAAACACCAG        3350

CAGCAGTTTT TCCAGTTCCG TTTATCCGGG CAAACCATCG AAGTGACCAG        3400

CGAATACCTG TTCCGTCATA GCGATAACGA GCTCCTGCAC TGGATGGTGG        3450

CGCTGGATGG TAAGCCGCTG GCAAGCGGTG AAGTGCCTCT GGATGTCGCT        3500

CCACAAGGTA AACAGTTGAT TGAACTGCCT GAACTACCGC AGCCGGAGAG        3550

CGCCGGGCAA CTCTGGCTCA CAGTACGCGT AGTGCAACCG AACGCGACCG        3600

CATGGTCAGA AGCCGGGCAC ATCAGCGCCT GGCAGCAGTG GCGTCTGGCG        3650

GAAAACCTCA GTGTGACGCT CCCCGCCGCG TCCCACGCCA TCCCGCATCT        3700

GACCACCAGC GAAATGGATT TTTGCATCGA GCTGGGTAAT AAGCGTTGGC        3750

AATTTAACCG CCAGTCAGGC TTTCTTTCAC AGATGTGGAT TGGCGATAAA        3800

AAACAACTGC TGACGCCGCT GCGCGATCAG TTCACCCGTG CACCGCTGGA        3850

TAACGACATT GGCGTAAGTG AAGCGACCCG CATTGACCCT AACGCCTGGG        3900

TCGAACGCTG GAAGGCGGCG GGCCATTACC AGGCCGAAGC AGCGTTGTTG        3950

CAGTGCACGG CAGATACACT TGCTGATGCG GTGCTGATTA CGACCGCTCA        4000

CGCGTGGCAG CATCAGGGGA AAACCTTATT TATCAGCCGG AAAACCTACC        4050

GGATTGATGG TAGTGGTCAA ATGGCGATTA CCGTTGATGT TGAAGTGGCG        4100

AGCGATACAC CGCATCCGGC GCGGATTGGC CTGAACTGCC AGCTGGCGCA        4150

GGTAGCAGAG CGGGTAAACT GGCTCGGATT AGGGCCGCAA GAAAACTATC        4200

CCGACCGCCT TACTGCCGCC TGTTTTGACC GCTGGGATCT GCCATTGTCA        4250

GACATGTATA CCCCGTACGT CTTCCCGAGC GAAAACGGTC TGCGCTGCGG        4300

GACGCGCGAA TTGAATTATG GCCCACACCA GTGGCGCGGC GACTTCCAGT        4350

TCAACATCAG CCGCTACAGT CAACAGCAAC TGATGGAAAC CAGCCATCGC        4400

CATCTGCTGC ACGCGGAAGA AGGCACATGG CTGAATATCG ACGGTTTCCA        4450

TATGGGGATT GGTGGCGACG ACTCCTGGAG CCCGTCAGTA TCGGCGGAAT        4500

TACAGCTGAG CGCCGGTCGC TACCATTACC AGTTGGTCTG GTGTCAAAAA        4550
```

-continued

| | | |
|---|---|---|
| TAATAATAAC CGGGCAGGCC ATGTCTGCCC GTATTTCGCG TAAGGAAATC | 4600 |
| CATTATGTAC TATTTAAAAA ACACAAACTT TTGGATGTTC GGTTTATTCT | 4650 |
| TTTTCTTTTA CTTTTTTATC ATGGGAGCCT ACTTCCCGTT TTTCCCGATT | 4700 |
| TGGCTACATG ACATCAACCA TATCAGCAAA AGTGATACGG GTATTATTTT | 4750 |
| TGCCGCTATT TCTCTGTTCT CGCTATTATT CCAACCGCTG TTTGGTCTGC | 4800 |
| TTTCTGACAA ACTCGGCCTC GACTCTAGGC GGCCGCGGGG ATCCAGACAT | 4850 |
| GATAAGATAC ATTGATGAGT TTGGACAAAC CACAACTAGA ATGCAGTGAA | 4900 |
| AAAAATGCTT TATTTGTGAA ATTTGTGATG CTATTGCTTT ATTTGTAACC | 4950 |
| ATTATAAGCT GCAATAAACA AGTTAACAAC AACAATTGCA TTCATTTTAT | 5000 |
| GTTTCAGGTT CAGGGGGAGG TGTGGGAGGT TTTTTCGGAT CCTCTAGAGT | 5050 |
| CGAGTAGATA AGTAGCATGG CGGGTTAATC ATTAACTACA AGGAACCCCT | 5100 |
| AGTGATGGAG TTGGCCACTC CCTCTCTGCG CGCTCGCTCG CTCACTGAGG | 5150 |
| CCGGGCGACC AAAGGTCGCC CGACGCCCGG GCTTTGCCCG GCGGCCTCA | 5200 |
| GTGAGCGAGC GAGCGCGCAG CAGATCTGGA AGGTGCTGAG GTACGATGAG | 5250 |
| ACCCGCACCA GGTGCAGACC CTGCGAGTGT GGCGGTAAAC ATATTAGGAA | 5300 |
| CCAGCCTGTG ATGCTGGATG TGACCGAGGA GCTGAGGCCC GATCACTTGG | 5350 |
| TGCTGGCCTG CACCCGCGCT GAGTTTGGCT CTAGCGATGA AGATACAGAT | 5400 |
| TGAGGTACTG AAATGTGTGG GCGTGGCTTA AGGGTGGGAA AGAATATATA | 5450 |
| AGGTGGGGGT CTTATGTAGT TTTGTATCTG TTTTGCAGCA GCCGCCGCCG | 5500 |
| CCATGAGCAC CAACTCGTTT GATGGAAGCA TTGTGAGCTC ATATTTGACA | 5550 |
| ACGCGCATGC CCCCATGGGC CGGGGTGCGT CAGAATGTGA TGGGCTCCAG | 5600 |
| CATTGATGGT CGCCCCGTCC TGCCCGCAAA CTCTACTACC TTGACCTACG | 5650 |
| AGACCGTGTC TGGAACGCCG TTGGAGACTG CAGCCTCCGC CGCCGCTTCA | 5700 |
| GCCGCTGCAG CCACCGCCCG CGGGATTGTG ACTGACTTTG CTTTCCTGAG | 5750 |
| CCCGCTTGCA AGCAGTGCAG CTTCCCGTTC ATCCGCCCGC GATGACAAGT | 5800 |
| TGACGGCTCT TTTGGCACAA TTGGATTCTT TGACCCGGGA ACTTAATGTC | 5850 |
| GTTTCTCAGC AGCTGTTGGA TCTGCGCCAG CAGGTTTCTG CCCTGAAGGC | 5900 |
| TTCCTCCCCT CCCAATGCGG TTTAAAACAT AAATAAAAAA CCAGACTCTG | 5950 |
| TTTGGATTTG GATCAAGCAA GTGTCTTGCT GTCTTTATTT AGGGGTTTTG | 6000 |
| CGCGCGCGGT AGGCCCGGGA CCAGCGGTCT CGGTCGTTGA GGGTCCTGTG | 6050 |
| TATTTTTTCC AGGACGTGGT AAAGGTGACT CTGGATGTTC AGATACATGG | 6100 |
| GCATAAGCCC GTCTCTGGGG TGGAGGTAGC ACCACTGCAG AGCTTCATGC | 6150 |
| TGCGGGGTGG TGTTGTAGAT GATCCAGTCG TAGCAGGAGC GCTGGGCGTG | 6200 |
| GTGCCTAAAA ATGTCTTTCA GTAGCAAGCT GATTGCCAGG GGCAGGCCCT | 6250 |
| TGGTGTAAGT GTTTACAAAG CGGTTAAGCT GGGATGGGTG CATACGTGGG | 6300 |
| GATATGAGAT GCATCTTGGA CTGTATTTTT AGGTTGGCTA TGTTCCCAGC | 6350 |
| CATATCCCTC CGGGGATTCA TGTTGTGCAG AACCACCAGC ACAGTGTATC | 6400 |
| CGGTGCACTT GGGAAATTTG TCATGTAGCT TAGAAGGAAA TGCGTGGAAG | 6450 |
| AACTTGGAGA CGCCCTTGTG ACCTCCAAGA TTTTCCATGC ATTCGTCCAT | 6500 |
| AATGATGGCA ATGGGCCCAC GGGCGGCGGC CTGGGCGAAG ATATTTCTGG | 6550 |

```
GATCACTAAC GTCATAGTTG TGTTCCAGGA TGAGATCGTC ATAGGCCATT      6600

TTTACAAAGC GCGGGCGGAG GGTGCCAGAC TGCGGTATAA TGGTTCCATC      6650

CGGCCCAGGG GCGTAGTTAC CCTCACAGAT TTGCATTTCC CACGCTTTGA      6700

GTTCAGATGG GGGGATCATG TCTACCTGCG GGGCGATGAA GAAAACGGTT      6750

TCCGGGGTAG GGGAGATCAG CTGGGAAGAA AGCAGGTTCC TGAGCAGCTG      6800

CGACTTACCG CAGCCGGTGG GCCCGTAAAT CACACCTATT ACCGGGTGCA      6850

ACTGGTAGTT AAGAGAGCTG CAGCTGCCGT CATCCCTGAG CAGGGGGGCC      6900

ACTTCGTTAA GCATGTCCCT GACTCGCATG TTTTCCCTGA CCAAATCCGC      6950

CAGAAGGCGC TCGCCGCCCA GCGATAGCAG TTCTTGCAAG GAAGCAAAGT      7000

TTTTCAACGG TTTGAGACCG TCCGCCGTAG GCATGCTTTT GAGCGTTTGA      7050

CCAAGCAGTT CCAGGCGGTC CCACAGCTCG GTCACCTGCT CTACGGCATC      7100

TCGATCCAGC ATATCTCCTC GTTTCGCGGG TTGGGCGGC TTTCGCTGTA       7150

CGGCAGTAGT CGGTGCTCGT CCAGACGGGC CAGGGTCATG TCTTTCCACG      7200

GGCGCAGGGT CCTCGTCAGC GTAGTCTGGG TCACGGTGAA GGGGTGCGCT      7250

CCGGGCTGCG CGCTGGCCAG GGTGCGCTTG AGGCTGGTCC TGCTGGTGCT      7300

GAAGCGCTGC CGGTCTTCGC CCTGCGCGTC GGCCAGGTAG CATTTGACCA      7350

TGGTGTCATA GTCCAGCCCC TCCGCGGCGT GGCCCTTGGC GCGCAGCTTG      7400

CCCTTGGAGG AGGCGCCGCA CGAGGGGCAG TGCAGACTTT TGAGGGCGTA      7450

GAGCTTGGGC GCGAGAAATA CCGATTCCGG GGAGTAGGCA TCCGCGCCGC      7500

AGGCCCCGCA GACGGTCTCG CATTCCACGA GCCAGGTGAG CTCTGGCCGT      7550

TCGGGGTCAA AAACCAGGTT TCCCCCATGC TTTTTGATGC GTTTCTTACC      7600

TCTGGTTTCC ATGAGCCGGT GTCCACGCTC GGTGACGAAA AGGCTGTCCG      7650

TGTCCCCGTA TACAGACTTG AGAGGCCTGT CCTCGACCGA TGCCCTTGAG      7700

AGCCTTCAAC CCAGTCAGCT CCTTCCGGTG GGCGCGGGGC ATGACTATCG      7750

TCGCCGCACT TATGACTGTC TTCTTTATCA TGCAACTCGT AGGACAGGTG      7800

CCGGCAGCGC TCTGGGTCAT TTTCGGCGAG GACCGCTTTC GCTGGAGCGC      7850

GACGATGATC GGCCTGTCGC TTGCGGTATT CGGAATCTTG CACGCCCTCG      7900

CTCAAGCCTT CGTCACTGGT CCCGCCACCA AACGTTTCGG CGAGAAGCAG      7950

GCCATTATCG CCGGCATGGC GGCCGACGCG CTGGGCTACG TCTTGCTGGC      8000

GTTCGCGACG CGAGGCTGGA TGGCCTTCCC CATTATGATT CTTCTCGCTT      8050

CCGGCGGCAT CGGGATGCCC GCGTTGCAGG CCATGCTGTC CAGGCAGGTA      8100

GATGACGACC ATCAGGGACA GCTTCAAGGA TCGCTCGCGG CTCTTACCAG      8150

CCTAACTTCG ATCACTGGAC CGCTGATCGT CACGGCGATT TATGCCGCCT      8200

CGGCGAGCAC ATGGAACGGG TTGGCATGGA TTGTAGGCGC CGCCCTATAC      8250

CTTGTCTGCC TCCCCGCGTT GCGTCGCGGT GCATGGAGCC GGGCCACCTC      8300

GACCTGAATG GAAGCCGGCG GCACCTCGCT AACGGATTCA CCACTCCAAG      8350

AATTGGAGCC AATCAATTCT TGCGGAGAAC TGTGAATGCG CAAACCAACC      8400

CTTGGCAGAA CATATCCATC GCGTCCGCCA TCTCCAGCAG CCGCACGCGG      8450

CGCATCTCGG GCAGCGTTGG GTCCTGGCCA CGGGTGCGCA TGATCGTGCT      8500
```

```
CCTGTCGTTG AGGACCCGGC TAGGCTGGCG GGGTTGCCTT ACTGGTTAGC        8550

AGAATGAATC ACCGATACGC GAGCGAACGT GAAGCGACTG CTGCTGCAAA        8600

ACGTCTGCGA CCTGAGCAAC AACATGAATG GTCTTCGGTT TCCGTGTTTC        8650

GTAAAGTCTG GAAACGCGGA AGTCAGCGCC CTGCACCATT ATGTTCCGGA        8700

TCTGCATCGC AGGATGCTGC TGGCTACCCT GTGGAACACC TACATCTGTA        8750

TTAACGAAGC CTTTCTCAAT GCTCACGCTG TAGGTATCTC AGTTCGGTGT        8800

AGGTCGTTCG CTCCAAGCTG GGCTGTGTGC ACGAACCCCC CGTTCAGCCC        8850

GACCGCTGCG CCTTATCCGG TAACTATCGT CTTGAGTCCA ACCCGGTAAG        8900

ACACGACTTA TCGCCACTGG CAGCAGCCAC TGGTAACAGG ATTAGCAGAG        8950

CGAGGTATGT AGGCGGTGCT ACAGAGTTCT TGAAGTGGTG GCCTAACTAC        9000

GGCTACACTA GAAGGACAGT ATTTGGTATC TGCGCTCTGC TGAAGCCAGT        9050

TACCTTCGGA AAAAGAGTTG GTAGCTCTTG ATCCGGCAAA CAAACCACCG        9100

CTGGTAGCGG TGGTTTTTTT GTTTGCAAGC AGCAGATTAC GCGCAGAAAA        9150

AAAGGATCTC AAGAAGATCC TTTGATCTTT TCTACGGGGT CTGACGCTCA        9200

GTGGAACGAA AACTCACGTT AAGGGATTTT GGTCATGAGA TTATCAAAAA        9250

GGATCTTCAC CTAGATCCTT TTAAATTAAA AATGAAGTTT TAAATCAATC        9300

TAAAGTATAT ATGAGTAAAC TTGGTCTGAC AGTTACCAAT GCTTAATCAG        9350

TGAGGCACCT ATCTCAGCGA TCTGTCTATT TCGTTCATCC ATAGTTGCCT        9400

GACTCCCCGT CGTGTAGATA ACTACGATAC GGGAGGGCTT ACCATCTGGC        9450

CCCAGTGCTG CAATGATACC GCGAGACCCA CGCTCACCGG CTCCAGATTT        9500

ATCAGCAATA AACCAGCCAG CCGGAAGGGC CGAGCGCAGA AGTGGTCCTG        9550

CAACTTTATC CGCCTCCATC CAGTCTATTA ATTGTTGCCG GGAAGCTAGA        9600

GTAAGTAGTT CGCCAGTTAA TAGTTTGCGC AACGTTGTTG CCATTGCTGC        9650

AGGCATCGTG GTGTCACGCT CGTCGTTTGG TATGGCTTCA TTCAGCTCCG        9700

GTTCCCAACG ATCAAGGCGA GTTACATGAT CCCCCATGTT GTGCAAAAAA        9750

GCGGTTAGCT CCTTCGGTCC TCCGATCGTT GTCAGAAGTA AGTTGGCCGC        9800

AGTGTTATCA CTCATGGTTA TGGCAGCACT GCATAATTCT CTTACTGTCA        9850

TGCCATCCGT AAGATGCTTT TCTGTGACTG GTGAGTACTC AACCAAGTCA        9900

TTCTGAGAAT AGTGTATGCG GCGACCGAGT TGCTCTTGCC CGGCGTCAAC        9950

ACGGGATAAT ACCGCGCCAC ATAGCAGAAC TTTAAAAGTG CTCATCATTG       10000

GAAAACGTTC TTCGGGGCGA AAACTCTCAA GGATCTTACC GCTGTTGAGA       10050

TCCAGTTCGA TGTAACCCAC TCGTGCACCC AACTGATCTT CAGCATCTTT       10100

TACTTTCACC AGCGTTTCTG GGTGAGCAAA AACAGGAAGG CAAAATGCCG       10150

CAAAAAAGGG AATAAGGGCG ACACGGAAAT GTTGAATACT CATACTCTTC       10200

CTTTTTCAAT ATTATTGAAG CATTTATCAG GGTTATTGTC TCATGAGCGG       10250

ATACATATTT GAATGTATTT AGAAAAATAA ACAAATAGGG GTTCCGCGCA       10300

CATTTCCCCG AAAAGTGCCA CCTGACGTCT AAGAAACCAT TATTATCATG       10350

ACATTAACCT ATAAAAATAG GCGTATCACG AGGCCCTTTC GTCTTCAA         10398
```

(2) INFORMATION FOR SEQ ID NO:2:

(i) SEQUENCE CHARACTERISTICS:
    (A) LENGTH: 4910 base pairs
    (B) TYPE: nucleic acid
    (C) STRANDEDNESS: double
    (D) TOPOLOGY: unknown (ii) MOLECULE TYPE: cDNA (xi) SEQUENCE DESCRIPTION: SEQ ID NO:2:

| | |
|---|---:|
| TCGCGCGTTT CGGTGATGAC GGTGAAAACC TCTGACACAT GCAGCTCCCG | 50 |
| GAGACGGTCA CAGCTTGTCT GTAAGCGGAT GCCGGGAGCA GACAAGCCCG | 100 |
| TCAGGGCGCG TCAGCGGGTG TTGGCGGGTG TCGGGCTGG CTTAACTATG | 150 |
| CGGCATCAGA GCAGATTGTA CTGAGAGTGC ACCATATGCG GTGTGAAATA | 200 |
| CCGCACAGAT GCGTAAGGAG AAAATACCGC ATCAGGCGCC ATTCGCCATT | 250 |
| CAGGCTGCGC AACTGTTGGG AAGGGCGATC GGTGCGGGCC TCTTCGCTAT | 300 |
| TACGCCAGCT GGCGAAAGGG GGATGTGCTG CAAGGCGATT AAGTTGGGTA | 350 |
| ACGCCAGGGT TTTCCCAGTC ACGACGTTGT AAAACGACGG CCAGTGCCAA | 400 |
| GCTTGCATGC CTGCAGGTCG ACTCTAGAGG ATCCGAAAAA ACCTCCCACA | 450 |
| CCTCCCCCTG AACCTGAAAC ATAAAATGAA TGCAATTGTT GTTGTTAACT | 500 |
| TGTTTATTGC AGCTTATAAT GGTTACAAAT AAAGCAATAG CATCACAAAT | 550 |
| TTCACAAATA AAGCATTTTT TTCACTGCAT TCTAGTTGTG GTTTGTCCAA | 600 |
| ACTCATCAAT GTATCTTATC ATGTCTGGAT CCCCGCGGCC GCCAAATCAT | 650 |
| TTATTGTTCA AAGATGCAGT CATCCAAATC CACATTGACC AGATCGCAGG | 700 |
| CAGTGCAAGC GTCTGGCACC TTTCCCATGA TATGATGAAT GTAGCACAGT | 750 |
| TTCTGATACG CCTTTTTGAC GACAGAAACG GGTTGAGATT CTGACACGGG | 800 |
| AAAGCACTCT AAACAGTCTT TCTGTCCGTG AGTGAAGCAG ATATTTGAAT | 850 |
| TCTGATTCAT TCTCTCGCAT TGTCTGCAGG GAAACAGCAT CAGATTCATG | 900 |
| CCCACGTGAC GAGAACATTT GTTTTGGTAC CTGTCTGCGT AGTTGATCGA | 950 |
| AGCTTCCGCG TCTGACGTCG ATGGCTGCGC AACTGACTCG CGCACCCGTT | 1000 |
| TGGGCTCACT TATATCTGCG TCACTGGGGG CGGGTCTTTT CTTGGCTCCA | 1050 |
| CCCTTTTTGA CGTAGAATTC ATGCTCCACC TCAACCACGT GATCCTTTGC | 1100 |
| CCACCGGAAA AAGTCTTTGA CTTCCTGCTT GGTGACCTTC CCAAAGTCAT | 1150 |
| GATCCAGACG GCGGGTGAGT TCAAATTTGA ACATCCGGTC TTGCAACGGC | 1200 |
| TGCTGGTGTT CGAAGGTCGT TGAGTTCCCG TCAATCACGG CGCACATGTT | 1250 |
| GGTGTTGGAG GTGACGATCA CGGGAGTCGG GTCTATCTGG GCCGAGGACT | 1300 |
| TGCATTTCTG GTCCACGCGC ACCTTGCTTC CTCCGAGAAT GGCTTTGGCC | 1350 |
| GACTCCACGA CCTTGGCGGT CATCTTCCCC TCCTCCCACC AGATCACCAT | 1400 |
| CTTGTCGACA CAGTCGTTGA AGGGAAAGTT CTCATTGGTC CAGTTTACGC | 1450 |
| ACCCGTAGAA GGGCACAGTG TGGGCTATGG CCTCCGCGAT GTTGGTCTTC | 1500 |
| CCGGTAGTTG CAGGCCCAAA CAGCCAGATG GTGTTCCTCT TGCCGAACTT | 1550 |
| TTTCGTGGCC CATCCCAGAA AGACGGAAGC CGCATATTGG GGATCGTACC | 1600 |
| CGTTTAGTTC CAAAATTTTA TAAATCCGAT TGCTGGAAAT GTCCTCCACG | 1650 |
| GGCTGCTGGC CCACCAGGTA GTCGGGGGCG GTTTTAGTCA GGCTCATAAT | 1700 |
| CTTTCCCGCA TTGTCCAAGG CAGCCTTGAT TTGGGACCGC GAGTTGGAGG | 1750 |

| | |
|---|---|
| CCGCATTGAA GGAGATGTAT GAGGCCTGGT CCTCCTGGAT CCACTGCTTC | 1800 |
| TCCGAGGTAA TCCCCTTGTC CACGAGCCAC CCGACCAGCT CCATGTACCT | 1850 |
| GGCTGAAGTT TTTGATCTGA TCACCGGCGC ATCAGAATTG GGATTCTGAT | 1900 |
| TCTCTTTGTT CTGCTCCTGC GTCTGCGACA CGTGCGTCAG ATGCTGCGCC | 1950 |
| ACCAACCGTT TACGCTCCGT GAGATTCAAA CAGGCGCTTA AATACTGTTC | 2000 |
| CATATTAGTC CACGCCCACT GGAGCTCAGG CTGGGTTTTG GGGAGCAAGT | 2050 |
| AATTGGGGAT GTAGCACTCA TCCACCACCT TGTTCCCGCC TCCGGCGCCA | 2100 |
| TTTCTGGTCT TTGTGACCGC GAACCAGTTT GGCAAAGTCG GCTCGATCCC | 2150 |
| GCGGTAAATT CTCTGAATCA GTTTTTCGCG AATCTGACTC AGGAAACGTC | 2200 |
| CCAAAACCAT GGATTTCACC CCGGTGGTTT CCACGAGCAC GTGCATGTGG | 2250 |
| AAGTAGCTCT CTCCCTTCTC AAATTGCACA AGAAAAGGG CCTCCGGGGC | 2300 |
| CTTACTCACA CGGCGCCATT CCGTCAGAAA GTCGCGCTGC AGCTTCTCGG | 2350 |
| CCACGGTCAG GGGTGCCTGC TCAATCAGAT TCAGATCCAT GTCAGAATCT | 2400 |
| GGCGGCAACT CCCATTCCTT CTCGGCCACC CAGTTCACAA AGCTGTCAGA | 2450 |
| AATGCCGGGC AGATGCCCGT CAAGGTCGCT GGGGACCTTA ATCACAATCT | 2500 |
| CGTAAAACCC CGGCATGGCG GCTGCGCGTT CAAACCTCCC GCTTCAAAAT | 2550 |
| GGAGACCCTG CGTGCTCACT CGGGCTTAAA TACCCAGCGT GACCACATGG | 2600 |
| TGTCGCAAAA TGTCGCAAAA CACTCACGTG ACCTCTAATA CAGGACTCTA | 2650 |
| GAGGATCCCC GGGTACCGAG CTCGAATTCG TAATCATGGT CATAGCTGTT | 2700 |
| TCCTGTGTGA AATTGTTATC CGCTCACAAT TCCACACAAC ATACGAGCCG | 2750 |
| GAAGCATAAA GTGTAAAGCC TGGGGTGCCT AATGAGTGAG CTAACTCACA | 2800 |
| TTAATTGCGT TGCGCTCACT GCCCGCTTTC CAGTCGGGAA ACCTGTCGTG | 2850 |
| CCAGCTGCAT TAATGAATCG GCCAACGCGC GGGGAGAGGC GGTTTGCGTA | 2900 |
| TTGGGCGCTC TTCCGCTTCC TCGCTCACTG ACTCGCTGCG CTCGGTCGTT | 2950 |
| CGGCTGCGGC GAGCGGTATC AGCTCACTCA AAGGCGGTAA TACGGTTATC | 3000 |
| CACAGAATCA GGGGATAACG CAGGAAAGAA CATGTGAGCA AAAGGCCAGC | 3050 |
| AAAAGGCCAG GAACCGTAAA AAGGCCGCGT TGCTGGCGTT TTTCCATAGG | 3100 |
| CTCCGCCCCC CTGACGAGCA TCACAAAAAT CGACGCTCAA GTCAGAGGTG | 3150 |
| GCGAAACCCG ACAGGACTAT AAAGATACCA GGCGTTTCCC CCTGGAAGCT | 3200 |
| CCCTCGTGCG CTCTCCTGTT CCGACCCTGC CGCTTACCGG ATACCTGTCC | 3250 |
| GCCTTTCTCC CTTCGGGAAG CGTGGCGCTT TCTCATAGCT CACGCTGTAG | 3300 |
| GTATCTCAGT TCGGTGTAGG TCGTTCGCTC CAAGCTGGGC TGTGTGCACG | 3350 |
| AACCCCCCGT TCAGCCCGAC CGCTGCGCCT TATCCGGTAA CTATCGTCTT | 3400 |
| GAGTCCAACC CGGTAAGACA CGACTTATCG CCACTGGCAG CAGCCACTGG | 3450 |
| TAACAGGATT AGCAGAGCGA GGTATGTAGG CGGTGCTACA GAGTTCTTGA | 3500 |
| AGTGGTGGCC TAACTACGGC TACACTAGAA GGACAGTATT TGGTATCTGC | 3550 |
| GCTCTGCTGA AGCCAGTTAC CTTCGGAAAA AGAGTTGGTA GCTCTTGATC | 3600 |
| CGGCAAACAA ACCACCGCTG GTAGCGGTGG TTTTTTTGTT TGCAAGCAGC | 3650 |
| AGATTACGCG CAGAAAAAAA GGATCTCAAG AAGATCCTTT GATCTTTTCT | 3700 |

-continued

| | | | | |
|---|---|---|---|---|
| ACGGGGTCTG | ACGCTCAGTG | GAACGAAAAC | TCACGTTAAG | GGATTTTGGT | 3750 |
| CATGAGATTA | TCAAAAAGGA | TCTTCACCTA | GATCCTTTTA | AATTAAAAAT | 3800 |
| GAAGTTTTAA | ATCAATCTAA | AGTATATATG | AGTAAACTTG | GTCTGACAGT | 3850 |
| TACCAATGCT | TAATCAGTGA | GGCACCTATC | TCAGCGATCT | GTCTATTTCG | 3900 |
| TTCATCCATA | GTTGCCTGAC | TCCCCGTCGT | GTAGATAACT | ACGATACGGG | 3950 |
| AGGGCTTACC | ATCTGGCCCC | AGTGCTGCAA | TGATACCGCG | AGACCCACGC | 4000 |
| TCACCGGCTC | CAGATTTATC | AGCAATAAAC | CAGCCAGCCG | GAAGGGCCGA | 4050 |
| GCGCAGAAGT | GGTCCTGCAA | CTTTATCCGC | CTCCATCCAG | TCTATTAATT | 4100 |
| GTTGCCGGGA | AGCTAGAGTA | AGTAGTTCGC | CAGTTAATAG | TTTGCGCAAC | 4150 |
| GTTGTTGCCA | TTGCTACAGG | CATCGTGGTG | TCACGCTCGT | CGTTTGGTAT | 4200 |
| GGCTTCATTC | AGCTCCGGTT | CCCAACGATC | AAGGCGAGTT | ACATGATCCC | 4250 |
| CCATGTTGTG | CAAAAAAGCG | GTTAGCTCCT | TCGGTCCTCC | GATCGTTGTC | 4300 |
| AGAAGTAAGT | TGGCCGCAGT | GTTATCACTC | ATGGTTATGG | CAGCACTGCA | 4350 |
| TAATTCTCTT | ACTGTCATGC | CATCCGTAAG | ATGCTTTTCT | GTGACTGGTG | 4400 |
| AGTACTCAAC | CAAGTCATTC | TGAGAATAGT | GTATGCGGCG | ACCGAGTTGC | 4450 |
| TCTTGCCCGG | CGTCAATACG | GGATAATACC | GCGCCACATA | GCAGAACTTT | 4500 |
| AAAAGTGCTC | ATCATTGGAA | AACGTTCTTC | GGGGCGAAAA | CTCTCAAGGA | 4550 |
| TCTTACCGCT | GTTGAGATCC | AGTTCGATGT | AACCCACTCG | TGCACCCAAC | 4600 |
| TGATCTTCAG | CATCTTTTAC | TTTCACCAGC | GTTTCTGGGT | GAGCAAAAAC | 4650 |
| AGGAAGGCAA | AATGCCGCAA | AAAAGGGAAT | AAGGGCGACA | CGGAAATGTT | 4700 |
| GAATACTCAT | ACTCTTCCTT | TTTCAATATT | ATTGAAGCAT | TTATCAGGGT | 4750 |
| TATTGTCTCA | TGAGCGGATA | CATATTTGAA | TGTATTTAGA | AAAATAAACA | 4800 |
| AATAGGGGTT | CCGCGCACAT | TTCCCCGAAA | AGTGCCACCT | GACGTCTAAG | 4850 |
| AAACCATTAT | TATCATGACA | TTAACCTATA | AAAATAGGCG | TATCACGAGG | 4900 |
| CCCTTTCGTC | | | | | 4910 |